US008946275B2

(12) United States Patent
Curd et al.

(10) Patent No.: US 8,946,275 B2
(45) Date of Patent: Feb. 3, 2015

(54) TREATMENT OF CANCER USING HYPOXIA ACTIVATED PRODRUGS

(75) Inventors: John G. Curd, Burlingame, CA (US); Karen Curd, legal representative, Burlingame, CA (US); Stewart Kroll, Oakland, CA (US); Mark Matteucci, Portola Valley, CA (US); Charles P. Hart, Mountain View, CA (US); Jian-Xin Duan, South San Francisco, CA (US)

(73) Assignee: Threshold Pharmaceuticals, Inc., South San Francisco, CA (US)

( * ) Notice: Subject to any disclaimer, the term of this patent is extended or adjusted under 35 U.S.C. 154(b) by 518 days.

(21) Appl. No.: 13/125,303

(22) PCT Filed: Oct. 21, 2009

(86) PCT No.: PCT/US2009/061541
§ 371 (c)(1),
(2), (4) Date: Jul. 27, 2011

(87) PCT Pub. No.: WO2010/048330
PCT Pub. Date: Apr. 29, 2010

(65) Prior Publication Data
US 2013/0202716 A1    Aug. 8, 2013

Related U.S. Application Data

(60) Provisional application No. 61/244,172, filed on Sep. 21, 2009, provisional application No. 61/151,163, filed on Feb. 9, 2009, provisional application No. 61/150,700, filed on Feb. 6, 2009, provisional application No. 61/118,368, filed on Nov. 26, 2008, provisional application No. 61/107,253, filed on Oct. 21, 2008.

(51) Int. Cl.
| | | |
|---|---|---|
| A01N 57/00 | (2006.01) |
| A61K 31/675 | (2006.01) |
| A01N 57/26 | (2006.01) |
| A61K 31/66 | (2006.01) |
| A61K 9/00 | (2006.01) |
| A61K 31/337 | (2006.01) |
| A61K 31/4985 | (2006.01) |
| A61K 31/513 | (2006.01) |
| A61K 31/555 | (2006.01) |
| A61K 31/704 | (2006.01) |
| A61K 31/7068 | (2006.01) |
| A61K 33/24 | (2006.01) |
| A61K 45/06 | (2006.01) |
| A61K 47/26 | (2006.01) |
| A61K 31/519 | (2006.01) |

(52) U.S. Cl.
CPC .............. *A61K 31/675* (2013.01); *A61K 9/0019* (2013.01); *A61K 31/337* (2013.01); *A61K 31/4985* (2013.01); *A61K 31/513* (2013.01); *A61K 31/555* (2013.01); *A61K 31/704* (2013.01); *A61K 31/7068* (2013.01); *A61K 33/24* (2013.01); *A61K 45/06* (2013.01); *A61K 47/26* (2013.01); *A61K 31/519* (2013.01)
USPC .............. 514/398; 514/94; 514/138; 514/400

(58) Field of Classification Search
None
See application file for complete search history.

(56) References Cited

U.S. PATENT DOCUMENTS

| | | | |
|---|---|---|---|
| 6,649,193 B1 | 11/2003 | Colic | |
| 8,003,625 B2 * | 8/2011 | Matteucci et al. | .............. 514/94 |
| 2003/0091574 A1 | 5/2003 | Gevas et al. | |
| 2007/0117784 A1 | 5/2007 | Cleland et al. | |

FOREIGN PATENT DOCUMENTS

| | | | |
|---|---|---|---|
| WO | 00/25775 A1 | 5/2000 |
| WO | WO 2007002931 A2 * | 1/2007 |
| WO | 2007/041546 A2 | 7/2007 |
| WO | 2008/083101 A1 | 7/2008 |

OTHER PUBLICATIONS

International Search Report for PCT/US2009/061541 mailed Dec. 24, 2009, 2 pages.
International Preliminary Report on Patentability for PCT/US2009/061541, dated Apr. 26, 2011, 6 pages.
Duan et al., "Potent and Highly Selective Hypoxia-Activated Achiral Phosphoramidate Mustards as Anticancer Drugs", Journal of Medicinal Chemistry, Feb. 8, 2008, 51(8):2412-2420.
Dorie et al., "Modification of the antitumor activity of chemotherapeutic drugs by the hypoxic cytotoxic agent tirapazamine," Cancer Chemother Pharmacol, 1997, vol. 39, pp. 361-366.
Dorie et al., "Tumor-specific, Schedule-dependent Interaction between Tirapazamine (SR 4233) and Cisplatin," Cancer Research, Oct. 1993, vol. 53, pp. 4633-4636.

(Continued)

*Primary Examiner* — James D Anderson
*Assistant Examiner* — Stephanie Springer
(74) *Attorney, Agent, or Firm* — Kilpatrick Townsend & Stockton LLP

(57) ABSTRACT

Cancer can be treated by administration of a hypoxia-activated prodrug, such as TH-302, alone or in combination with other anticancer agents and/or radiation therapy. In combination therapy, the hypoxia-activated prodrug and another anticancer agent or radiation therapy may be administered within the same 24-hour period, and administration of the hypoxia-activated prodrug may be completed prior to beginning administration of the other anticancer agent or radiation therapy.

18 Claims, No Drawings

(56) References Cited

OTHER PUBLICATIONS

Gallagher et al., "The chemopotentiation of cisplatin by the novel bioreductive drug AQ4N," British Journal of Cancer, 2001, vol. 84(4), pp. 625-629.

McKeown et al., "Bioreductive Drugs: from Concept to Clinic," Clinical Oncology, 2007, vol. 19, pp. 427-442.

Wang et al., "In vivo anti-cancer efficacy of a hypoxia activated prodrug, TH-302," Apr. 2007, American Association for Cancer Research, pp. 943-944 (Abstract).

European Application No. 09822657.4-1464, Supplementary European Search Report, Mar. 27, 2014, 5 pages.

\* cited by examiner

TREATMENT OF CANCER USING HYPOXIA ACTIVATED PRODRUGS

RELATED APPLICATIONS

This application claims priority to the following U.S. Provisional Applications: No. 61/107,253 (filed 21 Oct. 2008); No. 61/118,368 (filed 26 Nov. 2008); No. 61/150,700 (filed 6 Feb. 2009); No. 61/151,163 (filed 9 Feb. 2009); and No. 61/244,172 (filed 21 Sep. 2009). The entire disclosures of the aforementioned applications are incorporated herein by reference.

FIELD OF THE INVENTION

The present invention provides methods and compositions for treating cancer with hypoxia activated prodrugs administered alone and in combination with anticancer drugs that are not hypoxically activated and/or in combination with radiation therapy. The invention relates to the fields of medicine, pharmacology, and medicinal chemistry.

BACKGROUND OF THE INVENTION

Cancer is one of the major causes of human morbidity and mortality. Cancer treatment is challenging because it is difficult to kill cancer cells without damaging or killing normal cells. Damaging or killing normal cells during cancer treatment causes adverse side effects in patients and can limit the amount of anticancer drug administered to a cancer patient. It is also difficult to kill cancer cells in regions distant from the vasculature where anticancer drugs fail to penetrate.

Many cancer cells are more hypoxic relative to normal cells. Tumor hypoxia is associated with resistance to anticancer therapies, cancer relapse, and poor prognosis. Certain drugs in preclinical and clinical development target hypoxic cancer cells. These drugs, called hypoxia-activated prodrugs or "HAPs" are administered in an inactive, or prodrug, form but are activated, and become toxic, in a hypoxic environment. PCT Pat. Pub. Nos. WO 07/002,931 and WO 08/083,101, each of which is incorporated herein by reference, describe HAPs such as those having a structure defined by Formula I, below.

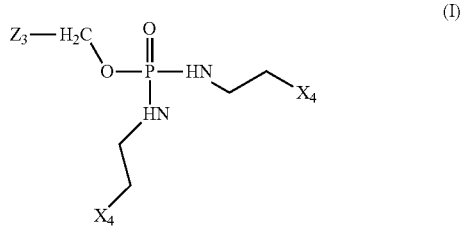

(I)

where $Z_3$ is selected from the group consisting of:

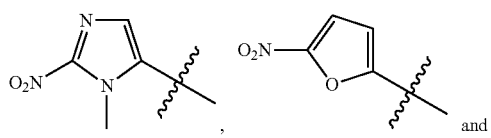

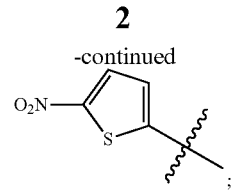

and $X_4$ is Cl or Br. The compounds known as TH-302 and TH-281 are particularly promising therapeutic candidates. TH-302, known by the chemical name (2-bromoethyl)({[(2-bromoethyl)amino][(2-nitro-3-methyl imidazol-4-yl)methoxy]phosphoryl})amine, has the structure represented below:

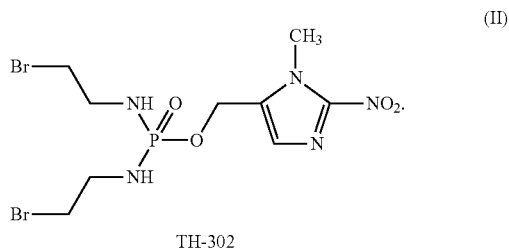 [SMILES: Cn1c(COP(=O)(NCCBr)NCCBr)cnc1[N+](=O)[O-]]

TH-302

See Duan et al., 2008, "Potent and highly selective hypoxia-activated achiral phosphoramidate mustards as anticancer drugs," *J Med. Chem.* 51: 2412, incorporated herein by reference. Another promising HAP is TH-281, which differs from TH-302 only in that it has 2-chloroethyl groups instead of the 2-bromoethyl groups present in TH-302.

There remains a need for new methods of formulating HAPs such as TH-302 and TH-281 to improve their anticancer efficacy as well as methods for administering them, and other HAPs, alone and in combination with other anticancer agents, to improve cancer therapy. The present invention meets these needs.

SUMMARY OF THE INVENTION

In one aspect, the present invention provides a stable liquid composition comprising TH-302 or another compound of Formula I (10 mg/mL to about 300 mg/mL), ethanol (70%-95%), a nonionic surfactant such as TWEEN 80 (5%-10%), and optionally one or more other agents, such as dimethylacetamide.

In another aspect, the present invention provides methods for treating cancer in a patient with TH-302 or another compound of Formula I, which methods comprise administering to a patient in need of cancer therapy TH-302 or another compound of Formula I as a single agent (i.e., in monotherapy, where no other anticancer agents are administered during the course of therapy with TH-302 or other compound of Formula I) at a dose in the range of 240 mg/m² to 1 g/m². In one embodiment, the therapeutically effective dose is administered once per week for at least three weeks. In one embodiment, the therapeutically effective dose is administered once per week for three weeks, no dose is administered during the fourth week (four weeks being one "cycle"), and this pattern of administration is followed for one or more additional cycles. In one embodiment, the therapeutically effective dose is administered once every three weeks, and this pattern of administration is followed for one or more additional cycles. In various embodiments, the dose administered once per week is 480 mg/m², 575 mg/m², or 670 mg/m². In various embodiments, the cancer is small cell lung cancer (SCLC), including but not limited to refractory SCLC, or melanoma. In one aspect the invention provides a method of treating cancer by administering TH-302 as a single agent, wherein said TH-302 is administered intravenously in an amount in the range of 200 mg/m$^2$ to 700 mg/m$^2$ to a patient in need of cancer therapy, e.g., treatment for a small cell lung cancer or melanoma.

In one aspect, the invention provides administering TH-302 monotherapy to a patient with small cell lung cancer. In some embodiments the TH-302 is administered once per week for 3 weeks followed by one week with no administration (e.g., days 1, 8 and 15 of a 28-day cycle). In some embodiments the TH-302 is administered to a patient with small cell lung cancer once per week for 3 weeks followed by one week with no administration at a dose in the range of about 480 mg/m$^2$-about 670 mg/m$^2$. In some embodiments the TH-302 is administered for at least 2, at least 3, at least 4, at least 5, or at least 6 28-day cycles. In some embodiments the TH-302 is administered once every three weeks (e.g., day 1 of a 21-day cycle). In some embodiments the TH-302 is administered to a patient with small cell lung cancer once every 3 weeks at a dose in the range of about 670 mg/m$^2$-less than 940 mg/m$^2$. In some embodiments the TH-302 is administered for at least 2, at least 3, at least 4, at least 5, or at least 6 21-day cycles.

In one aspect, the invention provides administering TH-302 monotherapy to a patient with metastatic melanoma. In some embodiments the TH-302 is administered once per week for 3 weeks followed by one week with no administration (e.g., days 1, 8 and 15 of a 28-day cycle). In some embodiments the TH-302 is administered at a dose in the range of about 480 mg/m$^2$-about 670 mg/m$^2$, sometimes about 575 mg/m$^2$-about 670 mg/m$^2$. In some embodiments the TH-302 is administered for at least 2, at least 3, at least 4, at least 5, or at least 6, 28-day cycles.

In another aspect, the present invention provides methods for treating cancer in which the patient is administered TH-302 (or another compound of Formula I) in combination with an oral and/or topical formulation of an agent to reduce or prevent mucosal and/or skin damage.

In another aspect, the present invention provides new methods for administering a hypoxia-activated prodrug (HAP) and a second anticancer agent that is not a HAP. According to these methods, the two drugs are administered noncontemporaneously, with administration of the non-HAP drug commencing a specified time after the completion of HAP administration.

In another aspect, the invention provides methods for treating cancer in which a patient in need of cancer therapy is administered TH-302 or another compound of Formula I in combination with a non-HAP anticancer agent. In various embodiments, the non-HAP anticancer agent is gemcitabine, docetaxel, pemetrexed, or doxorubicin. In various embodiments, the cancer is pancreatic cancer, prostate cancer, non-SCLC (NSCLC), or sarcoma. In one embodiment, the cancer is pancreatic cancer and the non-HAP anticancer agent is gemcitabine. In one embodiment, the cancer is prostate cancer, and the non-HAP anticancer agent is docetaxel. In one embodiment, the cancer is NSCLC, and the non-HAP anticancer agent is docetaxel or pemetrexed. In one embodiment, the cancer is sarcoma, and the non-HAP anticancer agent is doxorubicin.

In some aspects the invention provides a method of treating cancer by administering a therapeutically effective dose of TH-302 and a therapeutically effective dose of an anticancer drug that is not a hypoxia activated prodrug to a patient in need of cancer therapy, wherein (a) the patient is in need of treatment for NSCLC, prostate cancer, neuroendocrine cancer, anal cancer, urachal cancer, urethral cancer, breast cancer, melanoma, and renal cell carcinoma and the anticancer drug that is not a hypoxia activated prodrug is docetaxel; or (b) the patient is in need of treatment for bile duct cancer, ovarian cancer, esophageal cancer, pancreatic cancer, NSCLC, ampullary cancer, neuroendocrine cancer, soft tissue sarcoma, and thyroid cancer and the anticancer drug that is not a hypoxia activated prodrug is gemcitabine; or (c) the patient is in need of treatment for esophageal cancer, pancreatic cancer, NSCLC, neuroendocrine cancer, soft tissue sarcoma, colorectal cancer, hepatocellular carcinoma (HCC), renal cancer, and parotid cancer and the anticancer drug that is not a hypoxia activated prodrug is pemetrexed.

In some aspects the invention provides a method of treating cancer by administering TH-302 and a therapeutically effective dose of an anticancer drug that is not a hypoxia activated prodrug to a patient in need of cancer therapy, wherein TH-302 is administered intravenously in an amount in the range of 200 mg/m$^2$ to 500 mg/m$^2$ and administration of the anticancer drug that is not a hypoxia activated prodrug begins 30 minutes to 8 hours, optionally 2 hours to 6 hours, after administration of TH-302 is completed.

DETAILED DESCRIPTION OF THE INVENTION

This detailed description of the invention is divided into sections for the convenience of the reader. Section I provides definitions of certain terms used herein. Section II describes pharmaceutical formulations of TH-302, TH-281, and other compounds of Formula I provided by the invention. Section III describes methods for treating cancer with TH-302, TH-281, and other compounds of Formula I in single agent therapies (monotherapies) provided by the invention. Section IV describes methods for treating cancer with a HAP and non-HAP anticancer agents in combination. Section V describes methods for treating cancer with TH-302, TH-281, and other compounds of Formula I in combination with non-HAP anticancer agents. Section V is followed by examples that provide illustrative embodiments of the methods and compositions provided by the invention.

I. Definitions

The following definitions are provided to assist the reader. Unless otherwise defined, all terms of art, notations, and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not be construed as representing a substantial difference over the definition of the term as generally understood in the art.

"A," "an," and, "the" include plural referents unless the context clearly dictates otherwise. Thus, for example, reference to a compound refers to one or more compounds or at least one compound. As such, the terms "a" (or "an"), "one or more", and "at least one" are used interchangeably herein.

"About" as used herein is used to provide flexibility to a numerical range endpoint by providing that a given value may be "a little above" or "a little below" the endpoint accounting for variations one might see in measurements taken among different instruments, samples, and sample preparations. In one aspect, "about" refers to ±20% of a quantity and includes, but is not limited to, ±15%, ±10%, and ±5% of the quantity.

"Active agent" refers to a compound with a desired pharmacological effect and includes all pharmaceutically acceptable forms of the active agent described. For example, the active agent can be in an isomeric mixture, a solid complex bound to an ion exchange resin, or the like. In addition, the active agent can be in a solvated form. Active agent also includes all pharmaceutically acceptable salts, derivatives, and analogs of the active agent being described, as well as combinations thereof. For example, the pharmaceutically acceptable salts of the active agent may include, without limitation, the sodium, potassium, calcium, magnesium, ammonium, tromethamine, L-lysine, L-arginine, N-ethylglucamine, N-methylglucamine and salt forms thereof, as well as combinations thereof and the like. Any form of the active agent may be suitable for use in the compositions of the present invention, e.g., a pharmaceutically acceptable salt of the active agent, a free acid or free base of the active agent, or a mixture thereof.

"Administering" or "administration of" a drug to a patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

"Advanced solid tumor" refers to a solid tumor that has relapsed, progressed, metastasized after, and/or is refractory to, the initial or first line treatment. Advanced solid tumors include, but are not limited to, metastatic tumors in bone, brain, liver, lungs, lymph node, pancreas, prostate, and soft tissue (sarcoma).

"Cancer" refers to leukemias, lymphomas, carcinomas, and other malignant tumors of potentially unlimited growth that can expand locally by invasion and systemically by metastasis. Examples of cancers include, but are not limited to, cancer of the adrenal gland, bone, brain, breast, bronchi, colon and/or rectum, gallbladder, head and neck, kidneys, larynx, liver, lung, neural tissue, pancreas, prostate, parathyroid, skin, stomach, and thyroid. Certain other examples of cancers include, acute and chronic lymphocytic and granulocytic tumors, adenocarcinoma, adenoma, basal cell carcinoma, cervical dysplasia and in situ carcinoma, Ewing's sarcoma, epidermoid carcinomas, giant cell tumor, glioblastoma multiforma, hairy-cell tumor, intestinal ganglioneuroma, hyperplastic corneal nerve tumor, islet cell carcinoma, Kaposi's sarcoma, leiomyoma, leukemias, lymphomas, malignant carcinoid, malignant melanomas, malignant hypercalcemia, marfanoid habitus tumor, medullary carcinoma, metastatic skin carcinoma, mucosal neuroma, myeloma, mycosis fungoides, neuroblastoma, osteo sarcoma, osteogenic and other sarcoma, ovarian tumor, pheochromocytoma, polycythermia vera, primary brain tumor, small-cell lung tumor, squamous cell carcinoma of both ulcerating and papillary type, hyperplasia, seminoma, soft tissue sarcoma, retinoblastoma, rhabdomyosarcoma, renal cell tumor, topical skin lesion, veticulum cell sarcoma, and Wilm's tumor.

"Dose" and "dosage" refer to a specific amount of active or therapeutic agents for administration.

"Dosage form" refers to physically discrete units suitable as unitary dosages for human subjects and other mammals, each unit containing a predetermined quantity of active agent calculated to produce the desired onset, tolerability, and therapeutic effects, in association with one or more suitable pharmaceutical excipients such as carriers.

"Excipient" includes any inert substance combined with an active agent such as TH-302 to prepare a convenient dosage form and vehicle for delivering the active agent.

"Formulation" and "composition" are used interchangeably and refer to a mixture of two or more compounds, elements, or molecules. In some aspects the terms "formulation" and "composition" may be used to refer to a mixture of one or more active agents with a carrier or other excipients. A pharmaceutical formulation is suitable for administration to a human or mammal.

"Hyperproliferative disease" refers to a disease characterized by cellular hyperproliferation (e.g., an abnormally increased rate or amount of cellular proliferation), including cancer as well as other diseases, such as those where the hyperproliferation is part of an immune reaction, as occurs in autoimmune disorders. Examples of hyperproliferative diseases other than cancer include, but are not limited to, allergic angitis and granulomatosis (Churg-Strauss disease), asbestosis, asthma, atrophic gastritis, benign prostatic hyperplasia, bullous pemphigoid, coeliac disease, chronic bronchitis and chronic obstructive airway disease, chronic sinusitis, Crohn's disease, demyelinating neuropathies, dermatomyositis, eczema including atopic dermatitis, eustachean tube diseases, giant cell arteritis, graft rejection, hypersensitivity pneumonitis, hypersensitivity vasculitis (Henoch-Schonlein purpura), irritant dermatitis, inflammatory hemolytic anemia, inflammatory neutropenia, inflammatory bowel disease, Kawasaki's disease, multiple sclerosis, myocarditis, myositis, nasal polyps, nasolacrimal duct diseases, neoplastic vasculitis, pancreatitis, pemphigus vulgaris, primary glomerulonephritis, psoriasis, periodontal disease, polycystic kidney disease, polyarteritis nodosa, polyangitis overlap syndrome, primary sclerosing cholangitis, rheumatoid arthritis, serum sickness, surgical adhesions, stenosis or restenosis, scleritis, scleroderma, strictures of bile ducts, strictures (of duodenum, small bowel, and colon), silicosis and other forms of pneumoconiosis, type I diabetes, ulcerative colitis, ulcerative proctitis, vasculitis associated with connective tissue disorders, vasculitis associated with congenital deficiencies of the complement system, vasculitis of the central nervous system, and Wegener's granulomatosis.

"Hypoxia activated prodrug" or "HAP" refers to a prodrug wherein the prodrug is less active or inactive, relative to the corresponding drug, and comprises the drug and one or more bioreducible groups. HAPs include prodrugs that are activated by a variety of reducing agents and reducing enzymes, including without limitation single electron transferring enzymes (such as cytochrome P450 reductases) and two electron transferring (or hydride transferring) enzymes. In some embodiments, HAPs are 2-nitroimidazole triggered hypoxia-activated prodrugs. Examples of HAPs include, without limitation, TH-302, TH-281, PR104 and AQ4N. Methods of synthesizing TH-302 are described in PCT Pat. App. Pub. Nos. WO 07/002,931 and WO 08/083,101, incorporated herein by reference. Methods of synthesizing PR104 are described in US Pat. App. No. 2007/0032455, incorporated herein by reference. Other examples of HAPs are described, for example, in US Pat. App. Nos. 2005/0256191, 2007/0032455 and 2009/0136521 (each of which is incorporated herein by reference) and PCT Pat. App. Pub. Nos. WO 00/064864, WO 04/087075, and WO 07/002931 (incorporated herein by reference).

"Patient" and "subject" are used interchangeably to refer to a mammal in need of treatment for cancer or other hyperproliferative disease. Generally, the patient is a human. Generally, the patient is a human diagnosed with cancer. In certain embodiments a "patient" or "subject" may refer to a non-human mammal such as a non-human primate, a dog, cat, rabbit, pig, mouse or rat such as animals used in screening, characterizing, and evaluating drugs and therapies.

"Pharmaceutically acceptable carrier, excipient, or diluent" refers to a carrier, excipient, or diluent that is useful in preparing a pharmaceutical formulation that is generally safe, non-toxic, and neither biologically nor otherwise undesirable, and includes a carrier, excipient, or diluent that is acceptable for human pharmaceutical use and/or veterinary use. A "pharmaceutically acceptable carrier, excipient, or diluent" can refer to one or more than one such carrier, excipient, or diluent.

"Pharmaceutically acceptable salt" refers to salts of active agents that are prepared with relatively nontoxic acids. The compound of the present invention contains relatively basic functionalities, and acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogen-carbonic, phosphoric, monohydrogenphosphoric, dihydrogen-phosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M. et al., "Pharmaceutical Salts," *Journal of Pharmaceutical Science*, 66:119, 1977). Certain specific compounds of the present invention contain both basic and acidic functionalities that allow the compounds to be converted into either base or acid addition salts. The neutral forms of the compounds may be regenerated by contacting the salt with a base and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Prodrug" refers to a compound that, after administration, is metabolized or otherwise converted to a biologically active or more active compound (or drug) with respect to at least one property. A prodrug, relative to the drug, is modified chemically in a manner that renders it, relative to the drug, less active or inactive, but the chemical modification is such that the corresponding drug is generated by metabolic or other biological processes after the prodrug is administered. A prodrug may have, relative to the active drug, altered metabolic stability or transport characteristics, fewer side effects or lower toxicity, or improved flavor (for example, see the reference Nogrady, 1985, Medicinal Chemistry A Biochemical Approach, Oxford University Press, New York, pages 388-392, incorporated herein by reference). A prodrug may be synthesized using reactants other than the corresponding drug.

"QnD" or "qnd" refers to drug administration once every n days. For example QD (or qd) refers to once every day or once daily dosing, Q2D (or q2d) refers to a dosing once every two days, Q7D refers to a dosing once every 7 days or once a week, Q5D refers to dosing once every 5 days.

"Reduction" of a symptom or symptoms (and grammatical equivalents of this phrase) refers to decreasing the severity or frequency of the symptom(s), or elimination of the symptom(s).

"Solid tumor" refers to a cancer other than leukemia.

"$T_{1/2}$" refers to the "half-life" of a drug; i.e., the amount of time required for the concentration of a drug in, e.g., plasma, serum, or blood, to be halved. The $t_{1/2}$ of anticancer drugs that are not hypoxically activated are provided for example, in most recent editions of the PHYSICIANS' DESK REFERENCE, Medical Economics Company, Inc., Oradell, N.J.; and Goodman & Gilman's THE PHARMACOLOGICAL BASIS OF THERAPEUTICS", McGraw-Hill, New York and/or are discussed in the medical literature. The $t_{1/2}$ of hypoxically activated prodrugs can be found in the literature or determined using routine pharmacokinetic analysis methods.

"Therapeutically effective amount" of a drug refers to an amount of a drug that, when administered to a patient with cancer or other hyperproliferative disease, will have the intended therapeutic effect, e.g., alleviation, amelioration, palliation or elimination of one or more manifestations of cancer or another hyperproliferative disease in the patient. A therapeutic effect does not necessarily occur by administration of one dose, and may occur only after administration of a series of doses. Thus, a therapeutically effective amount may be administered in one or more administrations.

"Treating" or "treatment of" a condition or patient refers to taking steps to obtain beneficial or desired results, including clinical results. For purposes of this invention, beneficial or desired clinical results include, but are not limited to, alleviation or amelioration of one or more symptoms of cancer or other hyperproliferative disease; diminishment of extent of disease; delay or slowing of disease progression; amelioration, palliation, or stabilization of the disease state; or other beneficial results. Treatment of cancer may, in some cases, result in partial response or stable disease.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Abbreviations used in the description include:
CT—Computed tomography (CT)
D5W—5% dextrose in water
DLT—Dose limiting toxicity
HAP(s)—Hypoxia Activated Prodrug(s)
NSCLC—Non-Small Cell Lung Cancer
PD—Progressive disease PR—Partial response
RECIST—Response Evaluation Criteria In Solid Tumors
SCLC—Small Cell Lung Cancer
SD—Stable disease
SLD—Sum of the longest diameters
TGD—Tumor growth delay
TGI—Tumor growth inhibition

II. Pharmaceutical Formulations of Th-302 and Other Compounds of Formula I

TH-302, and other compounds of Formula I including TH-281, can be administered to patients in accord with the invention in any pharmaceutically acceptable formulation. For example, PCT Publications WO 08/083,101 and WO 07/002,931, both incorporated herein by reference, disclose methods for preparing liquid pharmaceutical formulations of TH-302 and other compounds of Formula I. WO 07/002,931 discloses that TH-302 can be provided as a lyophilized powder in a vial and reconstituted in saline or 5% dextrose in water (D5W) immediately prior to administration. After reconstitution in D5W, the TH-302 formulation must be used within 8 hours. The shelf life for this lyophilized TH-302 formulation is about 1 year at 2-8° C. WO 08/083,101 discloses that TH-302 can be administered as a liquid formulation in ethanol (containing up to 50 mg of TH-302 per ml). However, these prior art formulations have limitations in that they are not suitable for high concentrations of drug, and the stability (particularly with respect to keeping the active agent from precipitating) during long term storage and/or dilution of TH-302 is suboptimal.

The present inventors discovered that the poor aqueous solubility of the nitro-heteroaryl phosphoramide class of hypoxia-activated cancer drugs, such as TH-302, and other compounds of Formula I, can be improved by providing a nonionic surfactant for prolonged storage in an alcohol environment. This section describes certain preferred formulations containing ethanol and a nonionic surfactant such as TWEEN 80®. TWEEN 80 is sorbitan mono-oleate polyoxyethylene, CAS number 9005-65-6. Advantageously these preferred parenterally administrable pharmaceutical compositions provide improved stability and reduced degradation and precipitation for TH-302, as well as for other nitro-heteroaryl phosphoramide class hypoxia-activated cancer drugs with poor solubility, including TH-281, and other compounds of Formula I. In addition, these preferred formulations provide for a higher concentration of the active drug, e.g., TH-302, relative to other formulations that have been previously described. Because these liquid formulations are stable over the long term, no lyophilization of the drug is required, which eliminates the need to reconstitute a lyophilisate before use. Preferably, the pharmaceutically acceptable formulation is suitable for parenteral administration.

The present inventors have developed a concentrated, stable pharmaceutical composition and methods which can improve the stability of a poorly soluble nitro-heteroaryl phosphoramide class of hypoxia-activated cancer drug, such as TH-302 and other compounds of Formula I, by solubilizing and dispersing the drug within the solution for prolonged storage. In addition, including a nonionic surfactant in these formulations is useful for preventing precipitation and degradation of hypoxia-activated cancer drugs, particularly, TH-302 and TH-281, that may occur upon dilution with an aqueous media before administration.

Thus, according to the present invention, a stable TH-302 liquid formulation is provided as a mixture of a nonionic surfactant and a pharmaceutically acceptable alcohol. Preferably the alcohol is ethanol. Preferably the nonionic surfactant is TWEEN 80.

Ethanol is preferably included in an amount at least 70% of the mixture by volume. More preferably, the amount of alcohol used is at least about 70% to about 95% by volume, e.g., at least 70%, at least 80%, at least 90%, or at least about 95%.

In one embodiment, the TWEEN 80 or other nonionic surfactant is included in an amount of at least about 5% v/v of the mixture. For example, the nonionic surfactant can be included in an amount of about 5 to 10% of the formulation by volume. The nonionic surfactant helps inhibit precipitation of TH-302 out of the solution in the carrier. In addition, the nonionic surfactant may provide various other functions and advantages, such as acting as an antimicrobial or antibacterial agent.

Other exemplary nontoxic, nonionic surfactants suitable for use in the present invention include, but are not limited to, polysorbates (e.g., polyoxyethylene (20) sorbitan monolaurate, polyoxyethylene (20) sorbitan monopalmitate, polyoxyethylene (20) sorbitan monostearate and polyoxyethylene (20) sorbitan monooleate); alkylated aryl polyether alcohols known as TRITON®; polyethylene glycol tertdodecyl throether available as NONIC®; fatty and amide condensate or ALROSOL®; aromatic polyglycol ether condensate or NEUTRONYX®; fatty acid alkanolamine or NINOL® sorbitan monolaurate or SPAN®; polyoxyethylene sorbitan esters or TWEENs®; sorbitan monolaurate polyoxyethylene or TWEEN 20®; polyoxypropylene-polyoxyethylene or PLURONIC®; polyglycolyzed glycerides such as LABRASOL, and polyoxyethylated castor oil such as CREMOPHOR.

Typically, the liquid compositions of the present invention comprise from about 10 mg/ml to about 300 mg/ml of the active agent. One skilled in the art understands that the foregoing concentrations can be adjusted depending upon the particular active agent utilized and the amount of active agent desired in the final formulation. The amount of TH-302 included in the present liquid formulation is dictated by the intended use. Generally, the concentration of TH-302 will be in the range of 10 mg/ml to about 300 mg/ml or 30 mg/ml to about 300 mg/ml, more typically 50 mg/ml to 200 mg/ml, more usually 50 mg/ml to about 150 mg/ml, and even more usually 50 mg/ml to 125 mg/ml, and most usually greater than 50 mg/ml, such as about 60 mg/ml, 60 mg/ml to 100 mg/ml, 100 mg/ml to 150 mg/ml, 100 mg/ml to 200 mg/ml, or 100 mg/ml to about 300 mg/ml. These concentrations refer to the free base form of TH-302 or other agent; if TH-302 or other active agent is formulated or administered as a pharmaceutically acceptable salt or other form, the concentrations are adjusted so that an amount equivalent to the free base is used.

According to one embodiment, the carrier is ethanol, and the pharmaceutical formulation includes at least 5% v/v TWEEN 80. In one embodiment, the formulation comprises about 5 to 10% (v/v) TWEEN 80, 90-95% (v/v) ethanol, and about 50 mg/ml to 125 mg/ml TH-302, such as about 60 mg/ml TH-302. In one preferred embodiment, the formulation comprises about 5% TWEEN 80, about 95% ethanol, and about 60 mg/ml TH-302.

Thus, in an embodiment, the active agent in the formulation is TH-302, including all pharmacologically acceptable forms. In one aspect, the invention provides a liquid composition, wherein the active agent is TH-302 in its non-salt form. In other embodiments, the active agent is TH-281, optionally in its non-salt form, or another compound of Formula I. In the embodiments of the invention, the active agent can be provided for dissolution into the formulation of the invention in any suitable form. For example, it can be in the form of a powder, pellet, or a granule (i.e., an aggregate of smaller units of active agent). Any pharmaceutical grade of TH-302 or other compound of Formula I may be used.

Advantageously, chemical degradation is minimized in the formulations of the present invention. Thus it has been unexpectedly found that the present formulation comprising a nonionic surfactant provides a long-term stability characterized by TH-302 degradation of 15% or less over a period of 31 days or less at about −20° C. to about 25° C. See Example 1, infra. Typically a formulation comprising a nonionic surfactant (e.g., TWEEN 80) provides a long-term stability characterized by TH-302 degradation of 5% or less over a period of 31 days or less at about −20° C.

Furthermore, advantageously the TH-302 liquid formulation produced according to the present invention exhibits superior stability, where stability, in this instance, is characterized by TH-302 remaining in solution, e.g., not precipitating during storage or upon thawing.

In some embodiments, the formulation may optionally further comprise other components described herein. Thus, in various embodiments of the pharmaceutical formulations of the invention, mixtures of carriers are used. When a second carrier (in addition to ethanol) is used, it is generally N,N-dimethylacetamide (DMA). When used, the amide carrier is preferably included in an amount up to about 20% of the formulation by volume. Preferably the amount of amide carrier used is about 10% to about 20% by volume. In some embodiments the formulation consists of ethanol and TH-302. In some embodiments the formulation consists of ethanol, DMA and TH-302.

The compositions of the present invention can additionally include an antioxidant, preserving agents such as methyl-, ethyl-, and propyl-hydroxy-benzoates, butylated hydroxytoluene, and butylated hydroxyanisole; opacifying agents and chelating agents. Suitable antioxidants and chelating agents, include for example, butylated hydroxyanisole (BHA), butylated hydroxytoluene (BHT), propyl gallate (PG), ascorbyl palmitate, disodium EDTA (ethylenediamine tetraacetic acid; also known as disodium edentate), EDTA, tartaric acid, citric acid, citric acid monohydrate, and sodium sulfite. In one embodiment, the foregoing compounds are included in the pharmaceutical formulations in amounts in the range of about 0.01% to about 5% w/w. In one specific embodiment, the pharmaceutical formulation includes BHA, BHT, or PG used at a range of about 0.02% to about 1% and disodium EDTA, citric acid, or citric acid monohydrate used at a range of about 2% to about 5%. In one embodiment, the pharmaceutical formulation includes BHA used at about 0.05% w/w.

Any suitable method can be used to mix the formulation comprising the active agent, alcohol carrier, and non-ionic surfactant. In one embodiment, the active agent, alcohol carrier, and non-ionic surfactant are combined, and the mixture is administered directly to the patient, optionally after dilution.

The liquid pharmaceutical formulations of the invention can be conveniently provided in dosage forms. Methods for preparing dosage forms of other liquid formulations are known, and it will be apparent to those skilled in the art upon consideration of the instant disclosure how to prepare suitable dosage forms of the pharmaceutical formulations of the invention. For example, a liquid dosage form of the present invention can be prepared according to the procedures set forth, for example, in *Remington: The Science and Practice of Pharmacy*, 20th Ed., Lippincott, Williams & Wilkins (2003), and similar publications. The dosage form to be administered will, in any event, contain a quantity of the active agent in a therapeutically effective amount for relief of the condition being treated when administered in accordance with the teachings of this invention.

The pharmaceutical formulations of the invention can be packaged in any packaging that facilitates stability of the drug formulation. The pharmaceutical formulations provided by this invention may be contained in a sterilized vessel such as syringes, vials, or ampoules of various sizes and capacities. The sterilized vessel may optionally contain between 1-50 ml, 1-25 ml, 1-20 ml, 1-10 ml or 1-5 ml of the formulations. Sterilized vessels maintain sterility of the pharmaceutical formulations, facilitate transportation and storage, and allow administration of the pharmaceutical formulations without prior sterilization step.

The present invention also provides a kit for administering the liquid formulation comprising the active agent to a host in need thereof. In one embodiment, the kit comprises the active agent (e.g., TH-302) and a carrier (e.g., ethanol), comprising the nonionic surfactant (e.g., TWEEN 80). Mixing the active agent into a solution comprising the carrier and the surfactant preferably results in the formation of a pharmaceutical formulation according to the present invention. For example, the kit may comprise a first vessel comprising a hypoxia-activated cancer drug in a solid form; and a vessel comprising a carrier that contains a nonionic surfactant; wherein adding the carrier to the solid drug results in the formation of a pharmaceutical formulation for administering the drug. Mixing the solid drug and carrier may optionally form a pharmaceutical formulation that comprises TH-302 in a concentration described above, e.g., about 60 mg/ml. For illustration, between 30 and 300 mg TH-302 per ml of the carrier, optionally between 50 and 200 mg, and between 100 mg and 150 mg per ml of the carrier and nonionic surfactant may be used.

The pharmaceutical formulations provided in vessels or kits may be in a form that is suitable for direct administration or may be in a concentrated form that requires dilution relative to what is administered to the patient. For example, pharmaceutical formulations, described in this invention, may be in a form that is suitable for direct administration via intravenous administration or may be in a concentrated form that is diluted prior to administration. In one embodiment, about 500 to 1200 mg of TH-302 in a formulation of the invention is administered to a patient over 30-60 minutes after dilution in D5W to about 500 ml total volume.

The compositions of the present invention are useful in therapeutic applications, e.g., for treating cancer. While the formulations of this invention may be delivered via various routes of administration, they are typically administered intravenously (e.g., by infusion) but any acceptable method may be used (e.g., intraarterially, via local delivery by catheter or stent, and the like).

In one embodiment, a hypoxia-activated cancer drug formulation is infused through a connector, such as a Y site connector, that has three arms, each connected to a tube. As an example, BAXTER® Y-connectors of various sizes can be used. A vessel containing hypoxia-activated cancer drug formulation is attached to a tube further attached to one arm of the connector. Infusion fluids, such as 0.9% sodium chloride, or 5% dextrose, or 5% glucose, or Lactated Ringer's, are infused through a tube attached to the other arm of the Y-site connector. The infusion fluids and hypoxia-activated cancer drug formulations are mixed inside the Y site connector. The resulting mixture is infused into the patient through a tube connected to the third arm of the Y site connector. The advantage of this administration approach over the prior art is that the hypoxia-activated cancer drug is mixed with infusion fluids before it enters the patient's body, thus reducing the time when decomposition of therapeutic formulations may occur due to contact with water. In some embodiments, the hypoxia-activated cancer drug is mixed less than 10, 5, 2 or 1 minutes before entering the patient's body. In some embodiments the hypoxia-activated cancer drug is mixed less than 8, 6, 4, 2 or 1 hours before entering the patient's body.

As noted above, pharmaceutical formulations according to the present invention provide the further advantage because the nonionic surfactant/alcohol solution can be readily mixed with water, D5W or saline, the formulations can be easily and readily further diluted just prior to administration. For example, the pharmaceutical formulations can be diluted with water, saline or D5W within the 8 hour period preceding administration to a patient.

In one embodiment, the infusion administration is performed after determining the mg dose for a patient by multiplying the patient's body surface area by the prescribed TH-302 dose. The appropriate number of vials (for example, 100 mg/vial) of TH-302 are removed from a −20° C. freezer and left in an ambient room condition for 30-60 minutes to allow vials to warm to room temperature. Each 100 mg vial is reconstituted with 25 ml sterile D5W and shaken well. The number of ml of reconstituted TH-302 required is calculated by multiplying the desired mg dose by 0.25 (e.g., a 1000 mg dose requires 250 ml). Prior to adding reconstituted TH-302 to a 500/1000 ml sterile D5W IV bag, the equivalent volume of TH-302 to be added to the bag is removed, so that when the reconstituted drug is added to the bag the total volume is 500/1000 ml.

Patients may be infused with hypoxia-activated cancer drug formulations for any therapeutically suitable time, e.g., about 15, 30, or 45 minutes or for 1, 2, 3, 4, 5 or more hours. The speed and volume of the infusion can be regulated according to the patient's needs. The regulation of the infusion of hypoxia-activated cancer drug formulations can be performed according to existing protocols. For illustration, Table 1 outlines exemplary dilution volumes and infusion times based on total dose administered for TH-302 (longer infusion times are permitted based on physician judgment of the time required to administer the infusion volume).

TABLE 1

| Total TH-302 Dose (mg) | Infusion Volume (ml) | Infusion Duration* (minutes) |
|---|---|---|
| <1000 | 500 | 30 |
| 1000 or higher | 1000 | 60 |

*Longer infusions are permitted based on investigator judgment on the length of time required to administer the infusion volume.

An individual patient's surface area can be determined using routine methods known to oncologists and other medical providers. For an adult human, a dose of 1 mg/m$^2$ of an active agent (drug)=about 1.7 mg of that agent or drug per patient (i.e., the prototypical adult human has 1.7 m$^2$ of surface area). Therefore, for example, 100 mg/m$^2$ of a drug=about 170 mg of that drug per patient.

As described in more detail below, the pharmaceutical formulations of the invention may be co-administered with other agents. Co-administration in the context of this invention is defined to mean the administration of more than one therapeutic agent in the course of a coordinated treatment to achieve an improved clinical outcome. Such co-administration may also be coextensive, that is, occurring during overlapping periods of time. The additional agent administered may be in any conventional form and may include infusion fluids, therapeutic compounds, nutritious fluids, anti-microbial fluids, buffering and stabilizing agents. Therapeutic compounds, in this context, include, but are not limited to, anti-neoplastic agents, alkylating agents, agents that are members of the retinoids superfamily, antibiotic agents, hormonal agents, plant-derived agents, biologic agents, interleukins, interferons, cytokines, immuno-modulating agents, and monoclonal antibodies. As discussed in detail in Section IV, when the additional agent is an anti-neoplastic drug in preferred embodiments administration of the two agents is non-contemporaneous.

Optionally, the TH-302 formulations of the present invention may be administered, or co-administered with a non-hypoxia activated anticancer agent, via local delivery. See Sections III-V, infra, and Examples. The formulation, dose, administration route, frequency, and such other modes of administration of various anticancer agents other than TH-302, such as docetaxel, doxorubicin, gemcitabine, and pemetrexed, administered in accordance with the present methods, are disclosed herein, available in medical literature, and/or known to one of skill in the art. Local delivery of the pharmaceutical formulations of this invention can be by a variety of techniques and structures that administer the pharmaceutical formulation at or near a desired site. Examples of local delivery techniques and structures are not intended to be limiting but rather as illustrative of the techniques and structures available. Examples include local delivery catheters, site-specific carriers, implants, direct injection, or direct applications.

Local delivery by a catheter allows the administration of a sequential combination of therapeutic agents and/or compositions directly to the desired site according to the methods of the invention. Examples of local delivery using a balloon catheter are described in EP 383 492 A2 and U.S. Pat. No. 4,636,195. Additional examples of local, catheter-based techniques and structures are disclosed in U.S. Pat. No. 5,049,132 and U.S. Pat. No. 5,286,254. Generally, the catheter is placed such that the therapeutic agents can be delivered at or near the desired site. Dosages delivered through the catheter can vary, according to determinations made by one of skill, but often are in amounts effective to create a cytotoxic or cytostatic effect at the desired site. Preferably, these total amounts are less than the total amounts for systemic administration of the pharmaceuticals of this invention, and are less than the maximum tolerated dose. Delivery of the pharmaceutical formulations of this invention through catheters preferably should be formulated to a viscosity that enables delivery through a small treatment catheter, and may be formulated with pharmaceutically acceptable additional ingredients (active and inactive).

Local delivery by an implant describes the placement of a matrix that contains the pharmaceutical formulations of this invention into the desired site. The implant may be deposited by surgery or other means. The implanted matrix releases the inventive combination of therapeutic agents and/or compositions by diffusion, chemical reaction, solvent activators, or other equivalent mechanisms. Examples are set forth in Langer, 1990, *Science* 249:1527-33. Often the implants may be in a form that releases the inventive combination of therapeutic agents and/or compositions over time; these implants are termed time-release implants. The material of construction for the implants will vary according to the nature of the implant and the specific use to which it will be put. For example, bio-stable implants may have a rigid or semi-rigid support structure, with inventive combination of therapeutic agents and/or composition delivery taking place through a coating or a porous support structure. Other implants may be made of a liquid that stiffens after being implanted or may be made of a gel. The amounts of inventive combination of therapeutic agents and/or composition present in or on the implant may be in an amount effective to treat cell proliferation generally, or a specific proliferation indication, such as the indications discussed herein.

The formulations of the present invention can be used to treat any type of cancer in a subject, particularly cancers containing substantial areas of hypoxic tissue. Such cancers include but are not limited to lung cancer (including small cell lung cancer and non-small cell lung cancer), breast cancer, colon cancer, head and neck cancer, ovarian cancer, pancreatic cancer, soft tissue sarcomas, and prostate cancer. The formulations of the invention can also be used to treat non-cancer hyperproliferative diseases.

TH-302 formulated as discussed above may be administered as monotherapy or in combination with administration of another anticancer agent(s). The formulation may be administered in conjunction with a therapeutic cancer treatment, including but not limited to surgery (e.g., in an adjuvant or neoadjuvant setting) or radiation.

III. Administration of Th-302 In Cancer Monotherapy

TH-302 can be administered as monotherapy, i.e., alone, not in combination with any other anticancer agent, to treat cancer. In preferred embodiments, TH-302 is administered as a monotherapy for the treatment of melanoma (including metastatic melanoma) or SCLC (including refractory SCLC). As discussed infra and in Example 2, TH-302 has exhibited remarkable anticancer activity when administered to patients diagnosed with melanoma or with SCLC.

TH-302 is usually administered intravenously (e.g., by infusion) for monotherapy. In some embodiments, a TH-302/ethanol/TWEEN 80 formulation discussed supra is diluted into D5W or saline for infusion. Although a variety of dosage schedules are possible, typically TH-302 is administered for one or more cycles of (a) once weekly for 3 consecutive weeks followed by a week of no TH-302 administration (e.g., administered on days 1, 8, and 15 of a 28 day cycle) referred to as a "4 week cycle"; (b) once per week; (c) once every three weeks; or (d) twice every three weeks (e.g., administered on days 1 and 8 of a 21-day cycle). For a dosing regimen comprising a "4 week cycle," TH-302 can be administered, for example, at a dose of 480 mg/m$^2$ to 670 mg/m$^2$, most preferably 480 mg/m$^2$ to 575 mg/m$^2$, preferably about 575 mg/m$^2$. For weekly administration, TH-302 can be administered once weekly at doses up to 575 mg/m$^2$. For once every three week administration, the dose can be up to 670 mg/m$^2$. For some patients, doses up to 940 mg/m$^2$ or higher can be administered once every 3 weeks. Other doses may be selected based on the patient's age, health and other factors.

In various embodiments of the present invention, the amount of TH-302 administered is about 670 mg/m$^2$, 575 mg/m$^2$, 560 mg/m$^2$, 480 mg/m$^2$, 360 mg/m$^2$, 240 mg/m$^2$, and 120 mg/m$^2$, when the TH-302 is administered intravenously (e.g., by infusion).

Like other anticancer agents, TH-302 is usually administered in multiple cycles. For example and not for limitation, TH-302 may be administered using a "4 week cycle" for from 1 to 13 cycles, from 1 to 7 cycles, or from 1 to 4 cycles. As a second example, TH-302 may be administered at a frequency of once every week for 3 to 52, 3 to 28, 3 to 6, or 3 to 8 cycles (weeks). As a third example, TH-302 may be administered at a frequency of once every three weeks for 3 to 52, 3 to 28, 3 to 6, or 3 to 8 weeks. It will be recognized by medical professionals that certain of these periods of TH-302 administration include one or more weeks of drug holidays during which no TH-302 is administered.

As noted, TH-302 has shown benefit in patients with metastatic melanoma. The historical response rate in first-line metastatic melanoma is about 10%, so the results of treatment with TH-302 are quite remarkable. Eleven subjects with metastatic melanoma have been treated with TH-302 monotherapy at initial doses of 575 mg/m$^2$ to 670 mg/m$^2$ as part of a 3 consecutive week dosing regimen repeated every 4 weeks. RECIST tumor assessments have been performed for eight subjects. Three of the eight subjects assessed have had partial responses and three of eight subjects have had stable disease. Four of the eight subjects continued on-study for additional dosing cycles. Two of the three subjects with a partial response continued on-study through at least Cycle 3 and Cycle 7. The other subject discontinued with clinical deterioration associated with neurological decline from brain metastases.

Eight subjects with SCLC have been treated with TH-302 monotherapy at initial doses of 480 mg/m$^2$ to 670 mg/m$^2$ as part of a 3 consecutive week dosing regimen repeated every 4 weeks (this excludes one subject dosed at 60 mg/m$^2$ during the initial dose escalation). RECIST tumor assessments were performed initially for seven subjects. Two of seven subjects had partial responses and another three of these same seven subjects had stable disease. The historical response rate in refractory SCLC is less than 10%, so, again, these results are quite remarkable. One of the seven subjects continued on-study for additional cycles of treatment.

After the MTD was established at 575 mg/m$^2$ for TH-302 monotherapy administered once per week for three weeks of a four week cycle, a once every three week TH-302 dosing regimen was initiated. Six subjects have been dosed at 940 mg/m$^2$ and two of six subjects have had a dose limiting toxicity. The MTD for the once every three week dosing is 670 mg/m$^2$ unless a dose between 670 mg/m$^2$ and 940 mg/m$^2$ is explored.

Other therapeutically effective doses of TH-302 for monotherapy are provided by the invention. In various embodiments, the therapeutically effective dose of TH-302 in the methods of treating cancer is in an amount in the range of about 100 mg/m$^2$-about 700 mg/m$^2$, 200 mg/m$^2$-about 700 mg/m$^2$, about 300 mg/m$^2$-about 600 mg/m$^2$, about 350 mg/m$^2$-about 550 mg/m$^2$, about 400 mg/m$^2$-about 500 mg/m$^2$, about 400 mg/m$^2$-about 600 mg/m$^2$, about 450 mg/m$^2$-about 550 mg/m$^2$, about 450 mg/m$^2$-about 575 mg/m$^2$, about 480 mg/m$^2$-about 670 mg/m$^2$, and about 670 mg/m$^2$-<940 mg/m$^2$. In another aspect, the present invention provides methods of treating cancer comprising administering TH-302 in an amount in the range of about 700 mg/m$^2$-about 1200 mg/m$^2$ or about 800 mg/m$^2$-about 1000 mg/m$^2$, particularly when prophylaxis against toxicity is provided, for example as discussed below. In some embodiments the therapeutically effective dose of TH-302 for monotherapy is about 200 mg/m$^2$-about 500 mg/m$^2$.

In one aspect, the invention provides administering TH-302 monotherapy to a patient with small cell lung cancer. In some embodiments the TH-302 is administered once per week for 3 weeks followed by one week with no administration (e.g., days 1, 8 and 15 of a 28-day cycle). In some embodiments the TH-302 is administered to a patient with small cell lung cancer once per week for 3 weeks followed by one week with no administration at a dose in the range of about 480 mg/m$^2$-about 670 mg/m$^2$. In some embodiments the TH-302 is administered for at least 2, at least 3, at least 4, at least 5, or at least 6 28-day cycles. In some embodiments the TH-302 is administered once every three weeks (e.g., day 1 of a 21-day cycle). In some embodiments the TH-302 is administered to a patient with small cell lung cancer once every 3 weeks at a dose in the range of about 670 mg/m²-less than 940 mg/m². In some embodiments the TH-302 is administered for at least 2, at least 3, at least 4, at least 5, or at least 6 21-day cycles.

In one aspect, the invention provides administering TH-302 monotherapy to a patient with metastatic melanoma. In some embodiments the TH-302 is administered once per week for 3 weeks followed by one week with no administration (e.g., days 1, 8 and 15 of a 28-day cycle). In some embodiments the TH-302 is administered at a dose in the range of about 480 mg/m²-about 670 mg/m², sometimes about 575 mg/m²-about 670 mg/m². In some embodiments the TH-302 is administered for at least 2, at least 3, at least 4, at least 5, or at least 6, 28-day cycles.

TH-302 has an attractive safety profile as monotherapy. It is well tolerated at relatively high doses and does not induce significant dose limiting myelosuppression. The dose limiting toxicities in a dose escalation study were mucositis with one grade 3 event involving the oral mucosa and one grade 3 event involving the gastrointestinal mucosa. TH-302 also produces a predictable skin rash that is dose proportional and reversible. The rash is typically grade 1 or grade 2 depending on the dose and increased in incidence starting at a weekly monotherapy dose of 480 mg/m². The skin rashes and mucosal toxicities observed in clinical trials are consistent with the underlying pharmacology of a hypoxia-activated prodrug, because both the normal skin and the superficial mucosa contain regions of significant hypoxia. In a clinical trial of patients receiving TH-302 (575 mg/m²) the rash has been managed proactively with subject education stressing the importance of personal hygiene including skin hygiene, keeping the skin dry and avoiding prolonged high pressure on skin regions, topical agents containing zinc oxide, anti-fungal agents, and anti-bacterial agents. Anecdotal reports from clinical sites show an apparent decrease in severity and duration of the skin toxicity. Similarly, prophylactic use of "Miracle Mouth Wash" (contains dexamethasone, diphenhydramine, nystatin, and tetracycline) seems to reduce the incidence and severity of the oral lesions. Thus, in one embodiment, the present invention provides methods for treating cancer in which the patient is administered TH-302 (or another compound of Formula I) in combination with an oral and/or topical formulation of a drug or other agent to prevent mucosal and/or skin damage. Preferably the drug or agent is administered prophylactically (prior to development of significant mucosal or skin damage). For example, and not for limitation, suitable topical agents include one or a combination of the following: topical agents containing zinc oxide, anti-fungal agents, anti-oxidants and/or anti-bacterial agents. Topical anti-oxidants available for use in humans include topical vitamin C, topical vitamin E, topical melatonin and combinations thereof (see Dreher and Maiback, 2001, "Protective Effects of Topical Antioxidants in Humans" *Oxidants and Antioxidants in Cutaneous Biology. Current Problems in Dermatology*. Basel, Karger 29:157-164). Topical DMSO may be used (see U.S. Pat. No. 6,060,083, incorporated herein by reference). Other agents include, for example, vitamin K analogs (see Pat. Pub. US 2009/0239952, incorporated herein by reference), topical Vitamin C, topical Vitamin E topical corticosteroids, menthol cream, topical minocycline; lotions such as clindamycin 2%/hydrocortisone 1%, glutamine solutions and melatonin. Systemic agents including anti-fungal agents (e.g., nystatin) and anti-bacterial agents (e.g., tetracycline) may be used.

In addition to administration of TH-302 for treatment of cancer, other compounds of Formula I, such as TH-281, and can be administered in monotherapy, in accord with the methods, doses, schedules and prophylaxis described herein in relation to TH-302.

IV. Administering Hap and Non-Hap Anticancer Agents In Combination Therapy

The present invention also provides methods for treating cancer by administering hypoxia activated prodrugs, including TH-302, to cancer patients, in combination with another anticancer drug, wherein the therapeutic efficacy of the combination treatment is maximized and the toxicity of the combination treatment minimized by administering the hypoxia activated prodrug ("HAP") and the other anticancer drug non-contemporaneously. See Example 3, infra. Administering two drugs a certain time period apart in accordance with the present invention is referred to as "non-contemporaneous administration" of the two drugs. Administering two drugs together or one immediately after the other (with no or less than a 30 minute delay between ceasing the administration of the first and initiating the administration of the second drug) is referred to as "contemporaneous administration" of the two drugs.

Thus, in one aspect, the present invention provides a method of treating cancer by administering two anticancer drugs, a hypoxia activated prodrug and an anticancer drug that is not hypoxically activated, to a patient in need of such treatment, wherein the non-HAP anticancer drug is administered at least about 30 minutes after the immediate prior administration of the hypoxia activated prodrug is stopped. In an embodiment, the second drug is administered 30 minutes to 8 hours after administration of the HAP drug has stopped. In another embodiments, the second drug is administered 1 to 6 hours after administration of the HAP drug has stopped (e.g., about 2 hours, about 3 hours or about 4 hours after administration of the HAP drug). In some embodiments, the duration of the time between administration of TH-302 and the non-HAP drug (e.g., docetaxel) is from 1 to 10 hours, from 2 to 6 hours, or from 3 to 5 hours. In exemplary embodiments, the non-HAP anticancer drug is administered 1 hour or longer (e.g., 1, 2, 4, or 6 hours) after administration of the HAP has stopped. Typically, at least a 2 hour delay is employed. Thus, generally, the time of administration of the non-HAP drug is at least 30 minutes to one hour, typically at least 2 hours, sometimes at least 4 hours, and in any event no more than 24 hours after administration of the HAP. In various embodiments, the delay between completion of the administration of the HAP and administration of the second agent is shorter than 8 hours; for example, the delay may be less than 6, less than 6, or less than 4, hours.

In another aspect, the present invention provides a method for treating cancer in a patient comprising administering a hypoxia activated prodrug in combination with another anticancer drug in which the HAP is administered first, and the delay between completing the administration of the HAP and beginning administration of the other anticancer drug is equal to about the $t_{1/2}$ of the HAP, or equal to at least the $t_{1/2}$ of the HAP, or equal to about twice the $t_{1/2}$ of the HAP, or equal to at least twice the $t_{1/2}$ of the HAP. In one embodiment the delay is in the range bounded by the $t_{1/2}$ of the HAP and twice the $t_{1/2}$ of the HAP.

In one embodiment, the HAP is TH-302, TH-281, or another compound of Formula I. In another embodiment the hypoxia activated prodrug is AQ4N. In one embodiment, the HAP is PR104 having a structure of formula shown below:

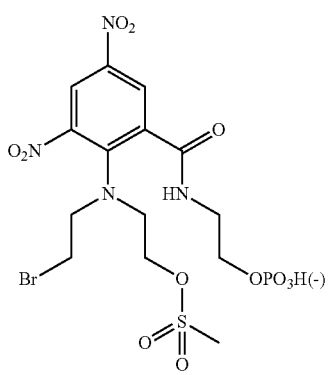

Pharmaceutically active salts of PR104 are also useful in accordance with the methods of the present invention. PR104 is a HAP for which the maximum tolerated dose (MTD) and recommended dose was determined, after a Phase I study, to be 1,100 mg/m$^2$. See, Jameson et al., *J. Clin. Oncol.*, 26: 2008 (May 20 suppl; abstr 2562; incorporated herein by reference). Phase II studies with PR104 were initiated by administering PR104 at 200-275 mg/m$^2$. See, Tchekmedyian et al., *J Clin Oncol* 26: 2008 (May 20 suppl.; abstr. 3575; incorporated herein by reference). However, when administered in combination with gemcitabine or docetaxel, the MTD of PR104 plus gemcitabine or docetaxel was 140 mg/m$^2$ for PR104 plus gemcitabine and <200 mg/m$^2$ for PR104 plus docetaxel. The methods of the present invention allow higher doses of HAPs to be administered in such combination therapies, including HAPs such as TH-302, TH-281, PR104, and AQ4N (see for example, PCT Pat. Pub. Nos. WO 00/064864, WO 04/087075, WO 07/002,931, and WO 08/083,101, and US Pat. App. Pub. No. 2007/0032455, each of which is incorporated herein by reference).

In another embodiment, the hypoxia activated prodrug is selected from the group consisting of the N-oxides of the vinca alkaloids. Certain N-oxides of the vinca alkaloids useful in the methods of the present invention are provided in the PCT patent publication No. WO 07/098,091, incorporated herein by reference. In one embodiment, the HAP is a compound described in any of PCT publication Nos. WO 2000/064864; 2004/087075; 2005/086951; 2005/087075; 2006/057946; 2007/002931; 2008/083101; 2008/151253; 2009/018163; and 2009/033165; PCT application No. US09/044038; US patent application publication Nos. 20050256191 and 20070032455; and U.S. provisional patent application No. 61/218,043, each of which is incorporated herein by reference. Routes, frequency, and such other parameters of administering therapeutically effective amounts of HAPs are described in these publications as well (see also Jameson et al., *J. Clin. Oncol.*, 26: 2008 (May 20 suppl.; abstr. 2562) and Tchekmedyian et al., *J. Clin. Oncol.* 26: 2008 (May 20 suppl.; abstr. 3575)). Other exemplary hypoxia activated prodrugs include benzotriazines, such as Tirapazamine (TPZ; SR4233; 1,2,4-benzotriazin-3-amine 1,4-dioxide), nitroaromatic compounds (e.g. misonidazole; 1-methyl-3-(2-nitro-1-imidazolyl)-2-propanol and RB 6145; 2-nitroimidazole) (see, e.g., Adams et al., 1994, *Int. J. Radiat. Oncol. Biol. Phys.* 29:231-38), anthraquinones (e.g. AQ4N; 1,4-Bis-[[2-(dimethylamino-N-oxide)ethyl]amino]5,8-dihydroxyanthracene-9,-10-dione) (see, e.g., Patterson, 1993, *Cancer Metastasis Rev.* 12:119-34; Patterson, 2002, *Drug Metab. Rev.* 34:581-92; Patterson et al., 2000, *Br. J. Cancer* 82:1984-90), the chloroquinoline DNA-targeting unit to 2-nitroimidazole (e.g. NLCQ-1; 4-[3-(2-Nitro-1-imidazolyl)-propylamino]-7-chloroquinoline hydrochloride) (see, e.g., Papadopoulou et al. 2003, *Clin. Cancer Res.* 9:5714-20), dinitrobenzamide mustards (e.g. SN 23862; 5-(N,N-bis(2-chloroethyl)amino)-2,4-dinitrobenzamide and SN 28343) (see, e.g., Siim et al., 1997, *Oncol. Res.* 9:357-69; Helsby, et al., 2003, *Chem. Res. Toxicol.* 16:469-78), nitrobenzyl phosphoramidate mustards (Nitroheterocyclic Phosphoramidates) (see, e.g., Borch et al., 2000, *J. Med. Chem.* 43:2258-65), nitrobeterocyclic methylquaternary salts (Nitroarylmethyl Quaternary Salts) (see, e.g., Tercel et al., 2001, *J. Med. Chem.* 44:3511-22), cobalt(III) complexes (see, e.g., Wilson et al., 1994, *Int. J. Radiat. Oncol. Biol. Phys.* 29:323-27) and indoloquinones (see, e.g., Everett et al., 2002, *Biochem. Pharmacol.* 63:1629-39), each incorporated by reference herein. In one embodiment, the HAP is not Tirapazamine or a Tirapazamine analog.

Cancer therapy typically involves multiple cycles of drug administration, and for many cancers, multiple drugs are administered. For illustration, and not for limitation, two anticancer drugs, A and B, may be administered in various administration sequences, as illustrated below:

i. ABAAABAAABAA (repeats or "cycles" of ABAA);
ii. ABAABAABAABA (cycles of ABA);
iii. ABABABABABABABAB (cycles of AB);
iv. ABBABBABBABBABB (cycles of ABB); and
v. ABBBABBBABBBABBB (cycles of ABBB).

Any of these (and other) cycles of administration can be employed in accordance with the present methods. For example, the sequence ABAAABAAABAA can represent 3 cycles in which "A" is TH-302 administered on Days 1, 8 and 15 of a 28 day cycle, and "B" is gemcitabine administered non-contemporaneously with A on Day 1 of the cycle. It will be understood that where there are multiple cycles and/or multiple administrations a drug(s) within a cycle, the delay between completing administration of HAP and initiation of administration of the non-HAP drug refers to the period between sequential administrations of HAP and non-HAP. For example, in a cycle $AB_1B_2B_3$ the period between completing administration of A and beginning administration of $B_1$ is measured (rather than, for example, the period between completing administration of A and beginning administration of $B_3$).

Hyperproliferative diseases other than cancer may also be treated using the methods of the invention.

In some embodiments, the anticancer drug that is not hypoxically activated is selected from the group consisting of platinum alkylators (cisplatin, carboplatin, oxaliplatin, and satraplatin), docetaxel, doxorubicin, gemcitabine, paclitaxel, 5-fluorouracil, and pemetrexed.

The anticancer drugs administered in accordance with the present invention can be administered via a variety of routes, including, without limitation IV and oral routes. Routes, frequency, and therapeutically effective amounts of administering anticancer drugs that are not hypoxia activated are provided, for example, in most recent editions of the PHYSICIANS' DESK REFERENCE, Medical Economics Company, Inc., Oradell, N.J.; and Goodman & Gilman's "THE PHARMACOLOGICAL BASIS OF THERAPEUTICS", McGraw-Hill, New York, Brown et al., *Cancer Lett.*, 1978, 5:291-97 (incorporated herein by reference), Yamada et al., *Cancer Lett.*, 2001, 172:17-25 (incorporated herein by reference), and/or are available from the Federal Drug Administration and/or are discussed in the medical literature.

In another aspect, the present invention provides a method of treating cancer and other hyperproliferative diseases, said method comprising administering a hypoxia activated prodrug and radiation therapy, to a patient in need of such treatment, wherein the HAP (e.g., TH-302) is administered from about 1 hour to about 48 hours, more typically about 1 to 24 hours before the radiation therapy is started. In one embodiment HAP treatment and radiation treatment both are administered within a 24 hour period, the HAP is administered first, and the radiation is administered at least about 30 minutes and no more than 24 hours after administration of the HAP is stopped. In one embodiment the lag between administration of the HAP and radiation treatment is 2-4 hours, such as about 2 hours or about 4 hours.

V. Combination Therapies with Th-302 In Combination with Other Anticancer Agents The present invention provides methods of treating cancer by administering TH-302 in combination with a second anticancer agent (other than a HAP) to a patient in need of such treatment.

As is discussed below, a wide variety of solid tumors and advanced solid tumors can be treated using such combination therapy, and a wide variety of anticancer agents can be administered in combination with TH-302 for therapeutic benefit. For example, clinical data show that the combination of TH-302 with gemcitabine has remarkable activity in first-line pancreatic cancer and the combinations of TH-302 with docetaxel or pemetrexed have remarkable activity in refractory non-small cell lung cancer (NSCLC). The combination of TH-302 with doxorubicin is very promising in soft tissue sarcoma.

Anticancer agents, which may be used in combination with TH-302, are well know. In certain embodiments the anticancer agent other than TH-302 is selected from the group consisting of docetaxel, doxorubicin, gemcitabine, and pemetrexed. See Tables 2 and 3, infra. In certain embodiments the anticancer agent other than TH-302 is selected from the group consisting of platinum alkylators (cisplatin, carboplatin, oxaliplatin, and satraplatin), docetaxel, doxorubicin, gemcitabine, paclitaxel, 5-fluorouracil, and pemetrexed.

Clinical observations to date support the following conclusions. In accordance with the methods of the invention, TH-302 can be broadly combined with commonly used standard chemotherapies particularly including gemcitabine, docetaxel, pemetrexed, and doxorubicin. The MTD of TH-302 in each of the combinations will likely be greater than 50% of the MTD of weekly TH-302 monotherapy. Broad activity has been observed with RECIST responses in all four of the combinations of TH-302 with gemcitabine, docetaxel, pemetrexed, and doxorubicin. Partial responses were observed at all TH-302 dose levels including at the lowest dose of TH-302 (240 mg/m$^2$) studied in the combinations. The response rates are considerably higher than one would expect based on prior studies in similar trials or in similar trials of specific tumors such as pancreatic cancer, recurrent NSCLC, and soft-tissue sarcoma. In addition, many of the responses are durable, thus providing well-defined clinical benefit for the subjects. The proportion of subjects with stable disease on treatment is also notable and the measure of clinical benefit described by the sum of partial responses (28%) and stable disease (51%) is nearly 80%.

TH-302 Administration for Combination Therapy

The formulation, dose, administration route, frequency, and such other modes of administration of TH-302 include those described herein below and those described in Section II, supra (discussing administration of TH-302 for monotherapy). One of ordinary skill in the art, upon reading this disclosure, will appreciate that in certain embodiments of the present invention, when administered as part of a combination treatment for cancer, TH-302 is typically administered in amounts lesser than those administered in TH-302 monotherapy. In preferred embodiments, administration of TH-302 and a second chemotherapeutic agent is conducted in accord with the methods described in Section IV, supra. That is, the drugs are administered non-contemporaneously, with the administration of the non-HAP beginning after administration of the TH-302. Typically administration of the non-HAP commences 30 min to 6 hours after completion of TH-302 administration (e.g., a delay of about 1, about 2, about 3, about 4, about 5, or about 6 hours). In some embodiments administration of the non-HAP commences about 2 hours after completion of TH-302 administration.

In preferred embodiments of the combination therapies of the invention, TH-302 is usually administered by IV infusion at a dose of 200 mg/m$^2$-500 mg/m$^2$. For example, in certain embodiments, when administered in combination with another anticancer agent, TH-302 is administered in an amount of about 120 mg/m$^2$, 240 mg/m$^2$, 340 mg/m$^2$, 400 mg/m$^2$, 480 mg/m$^2$, and 560 mg/m$^2$. The dose will depend, in part, on what chemotherapeutic agent other than TH-302 is used, as well as the patient's condition and cancer being treated. The MTD of TH-302 plus gemcitabine is anticipated to be 340-400 mg/m$^2$; the MTD of TH-302 plus docetaxel is 340 mg/m$^2$, and the MTD of TH-302 plus pemetrexed is 480 mg/m$^2$; and the MTD of TH-302 plus doxorubicin is anticipated to be 300 mg/m$^2$; in each case when the non-HAP drug is non-contemporaneously administered at conventional doses, e.g., as described below.

In various embodiments, TH-302 may be administered in combination with another agent in an amount in the range of about 100 mg/m$^2$-about 700 mg/m$^2$, about 300 mg/m$^2$-about 600 mg/m$^2$, about 350 mg/m$^2$-about 550 mg/m$^2$, about 400 mg/m$^2$-about 500 mg/m$^2$, about 400 mg/m$^2$-about 600 mg/m$^2$, about 450 mg/m$^2$-about 550 mg/m$^2$, about 200 mg/m$^2$-about 500 mg/m$^2$, or about 200 mg/m$^2$-575 mg/m$^2$.

In combination treatment of cancer, TH-302 may be administered according to a variety of schedules, including those described is administered for one or more 4 week cycles, as described above for TH-302 monotherapy (i.e., once per week for three weeks followed by one week without administering TH-302). In other embodiments of the present invention, for combination treatment of cancer, TH-302 is administered for one or more 3 week cycles. In a 3 week administration cycle, TH-302 can be administered once weekly for 2 consecutive weeks followed by a week of no TH-302 or, alternatively, can be administered once every 3 weeks. In certain embodiments of the present invention, for combination treatment of cancer, TH-302 is administered weekly. TH-302 may be administered once weekly for seven weeks followed by one week of no administration, followed by one or more 28-day cycles.

TH-302 is usually administered intravenously, typically by infusion. In some embodiments TH-302 is formulated with ethanol and TWEEN 80 as discussed in Section II, supra (discussing administration of TH-302 for monotherapy). In preferred embodiments TH-302 is administered prior to administration of the second, non-HAP anticancer agent, and administration of TH-302 is stopped at least 30 minutes to one hour (or at least 2-6 hours) before administration of the second, non-HAP anticancer agent is initiated, i.e., as described in Section III, supra. In one embodiment, the present invention provides methods of treating cancer comprising administering TH-302 intravenously, in combination with another anticancer agent to a patient in need of such treatment, where the TH-302 is administered in an amount of up to about 1000 mg/m². In some embodiments the dose of TH-302 used in a particular combination therapy and administration schedule is in the range bounded by the MTD for the particular schedule and combination and a dose equal to the MTD minus 100 mg/m² (i.e., in some embodiments the dose of TH-302 used in a particular combination therapy and administration schedule is dosed up to 100 mg/m² less than the MTD).

Treatable Cancers

A variety of solid tumors and advanced solid tumors can be treated in accordance with the present methods for combination therapy with TH-302. TH-302 may be administered in combination with one (or more) additional chemotherapeutic agents as an initial or first line treatment, for treatment of refractory or metastatic cancer, and as adjuvant or neoadjuvant therapy.

Thus, in one embodiment of the present invention, the cancer is treated, following diagnosis, in the neoadjuvant setting (chemotherapy is administered to the patient before surgery to shrink the primary tumor and facilitate removal of the primary tumor). In another embodiment, the combination therapy is administered, following diagnosis, as adjuvant treatment (chemotherapy is given after the tumor is removed and the patient is staged; if there is a high likelihood of recurrent then prophylactic chemotherapy is given to delay recurrence and improve survival). In another embodiment, the combination therapy is administered for treatment of refractory or metastatic cancer (chemotherapy is given for recurrence(s) or spread of the cancer).

Treatable cancers in accordance with the methods herein include, therefore, previously untreated cancers, a refractory cancer, and a metastatic cancer. In another embodiment of the present invention, the relapsed cancer, refractory cancer, or metastatic cancer treated is selected from the group consisting of lung cancer, liver cancer, prostate cancer and skin cancer.

The data across indications and dose groups for human patients treated to date are provided in Tables 2 and 3, below. Tumor responses reported across all dose groups and across all combinations suggest that TH-302 has activity in a broad range of tumor subtypes and in combination with a range of standard chemotherapies. Importantly, substantial doses of TH-302 can be combined with the approved full doses and full schedules of all standard chemotherapies in accordance with the methods of the invention.

TABLE 2

TH-302 Combination Therapy: Overall Efficacy by Tumor Type

| Cancer Type | TH-302 + gemcitabine mg/m² | | | | TH-302 + docetaxel mg/m² | | | TH-302 + pemetrexed mg/m² | | | | TH-302 + doxorubicin mg/m² | |
|---|---|---|---|---|---|---|---|---|---|---|---|---|---|
| | 240 | 340 | 480 | 575 | 240 | 340 | 480 | 240 | 340 | 480 | 575 | 240** | 340 |
| Bile Duct | SD | SD | | | | | | | | | | | |
| Ovarian | PD | | | | | | | | | | | | |
| | PR | | | | | | | | | | | | |
| Esophageal | PR | | | | | | | | | | PD | | |
| Pancreatic | | PR | SD | SD | | | | | | SD | | | |
| | | | PR | | | | | | | | | | |
| NSCLC | | | | PR | SD | PR | | PR-2 | SD | | PD | | |
| | | | | | | | | SD | | | SD | | |
| Prostate | | | | | | SD-2 | | | | | | | |
| Ampullary | | SD | | | | | | | | | | | |
| Neuro-endocrine | SD | | | | SD | | | | | SD | | | |
| Soft Tissue Sarcoma | | SD | | | | | | | | PD | | PR-2 | PR |
| | | | | | | | | | | | | SD-2 | PD |
| | | | | | | | | | | | | | SD |
| Colorectal | | | | | | | | SD | SD | | | | |
| | | | | | | | | PD | | | | | |
| Anal | | | | | PR | | | | | | | | |
| Urachal | | | | | SD | | | | | | | | |
| Urethral | | | | | PD | | | | | | | | |
| Breast | | | | | SD | | | | | | | | |
| Melanoma | | | | | | SD | SD | | | | | | |
| | | | | | | PD | | | | | | | |
| HCC | | | | | | | | | | SD | | | |
| Renal | | | | | | PD | | | | PR | PR | | |
| Thyroid | | | | PR | | | | | | | | | |
| Parotid | | | | | | | | | | SD | | | |
| Unknown 1° | | | | | | | | | PD-2 | | | | |

TABLE 3

TH-302 as Combination Therapy: Overall Efficacy

| TH-302 Weekly Dose (mg/m²) | Number of Subjects | Number with Tumor Assessment | Partial Response | Stable Disease | Progressive Disease |
|---|---|---|---|---|---|
| Gemcitabine | | | | | |
| 240 | 7 | 5 | 2 | 2 | 1 |
| 340 | 6 | 3 | 1 | 2 | 0 |
| 480 | 6 | 3 | 1 | 2 | 0 |
| 575 | 7 | 3 | 2 | 1 | 0 |
| Docetaxel | | | | | |
| 240 | 8 | 6 | 1 | 4 | 1 |
| 340 | 5 | 3 | 1 | 1 | 1 |
| 480 | 7 | 4 | 0 | 3 | 1 |
| Pemetrexed | | | | | |
| 240 | 5 | 5 | 2 | 2 | 1 |
| 340 | 6 | 2 | 0 | 2 | 0 |

TABLE 3-continued

TH-302 as Combination Therapy: Overall Efficacy

| TH-302 Weekly Dose (mg/m$^2$) | Number of Subjects | Number with Tumor Assessment | Partial Response | Stable Disease | Progressive Disease |
|---|---|---|---|---|---|
| 480 | 9 | 8 | 1 | 3 | 4 |
| 575 | 7 | 4 | 1 | 2 | 1 |
| Doxorubicin | | | | | |
| 240 | 6 | 4 | 2 | 2 | 0 |
| 340 | 4 | 3 | 1 | 1 | 1 |
| Total | 83 | 53 | 15 (28%) | 27 (51%) | 11 (21%) |

The data shown in Tables 2 and 3 demonstrate that the combination therapies of the invention are effective in treating a wide variety of cancers. Thus, methods of the invention include treatment of:

(a) NSCLC, prostate cancer, neuroendocrine cancer, anal cancer, urachal cancer, urethral cancer, breast cancer, melanoma, and renal cell carcinoma with TH-302 and docetaxel;

(b) bile duct cancer, ovarian cancer, esophageal cancer, pancreatic cancer, NSCLC, ampullary cancer, neuroendocrine cancer, soft tissue sarcoma, and thyroid cancer with TH-302 and gemcitabine; and (c) esophageal cancer, pancreatic cancer, NSCLC, neuroendocrine cancer, soft tissue sarcoma, colorectal cancer, hepatocellular carcinoma (HCC), renal cancer, and parotid cancer with TH-302 and pemetrexed.

In one embodiment of the present invention, TH-302 is administered in combination with docetaxel, the cancer treated is prostate cancer, and TH-302 is administered in an amount in the range of about 200 mg/m$^2$-500 mg/m$^2$, usually about 340 mg/m$^2$. In another embodiment of the present invention, TH-302 is administered in combination with doxorubicin, the cancer treated is soft tissue sarcoma, and TH-302 is administered in an amount in the range of about 200 mg/m$^2$-500 mg/m$^2$, e.g., 240 mg/m$^2$-340 mg/m$^2$. In another embodiment of the present invention, TH-302 is administered in combination with pemetrexed, the cancer treated is non small cell lung cancer (NSCLC), and TH-302 is administered in an amount in the range of about 200 mg/m$^2$-500 mg/m$^2$, usually about 400 mg/m$^2$. In another embodiment of the present invention, TH-302 is administered in combination with gemcitabine, the cancer treated is pancreatic cancer, and TH-302 is administered in an amount in the range of about 200 mg/m$^2$-500 mg/m$^2$, usually about 340-400 mg/m$^2$.

For combination therapy, TH-302 (or other compound of Formula I) can be administered at frequencies and durations described for TH-302 monotherapy above. Thus, in one embodiment of the present invention, the TH-302 is administered at a frequency of once every week. In another embodiment of the present invention, TH 302 is administered in multiple cycles, each cycle of administration being a 4 week cycle wherein, TH-302 is administered once weekly for 3 consecutive weeks. In this embodiment, for each administration cycle, TH-302 administered once weekly for 3 consecutive weeks is administered on days 1, 8, and 15, followed by a week of no drug administration, followed by a week of no TH-302 administration. In one embodiment of the present invention, the TH-302 is administered for a period in the range of 3 weeks-52 weeks, 3 weeks-28 weeks, 3 weeks-16 weeks, and 3 weeks-8 weeks. Thus, in accordance with the present methods, TH-302 can be administered, for example and without limitation, for 1-13, 1-7, or 1-4 cycles. Certain of these periods of TH-302 administration include one or more weeks of drug holidays during which no TH-302 is administered.

Administration of Anticancer Agents Other than TH-302

The formulation and dose, route, frequency, and such other modes of administration of various anticancer agents, other than TH-302, administered in accordance with the present methods, are disclosed herein, are available in medical literature, and/or are known to one of skill in the art. Thus, the doses of the non-TH-302 chemotherapeutic agent (e.g., gemcitabine, docetaxel, pemetrexed, doxorubicin, and others anticancer agents) are approved doses listed in their respective product labeling. The therapeutically effective amount of an anticancer agent other than TH-302 administered in accordance with the present methods, at least for known and approved anticancer agents, are known to physicians and are provided, for example and without limitation, in the product descriptions found in the PHYSICIANS' DESK REFERENCE, 2003, 57th Ed., Medical Economics Company, Inc., Oradell, N.J.; Goodman & Gilman's THE PHARMACOLOGICAL BASIS OF THERAPEUTICS" 2001, 10$^{th}$ Edition, McGraw-Hill, New York; and/or are available from the Federal Drug Administration and/or are discussed in the medical literature. Illustrative dosing amounts and schedules for various cancers in accordance with the methods of the invention are described herein.

For illustration and not for limitation, the following dosages and schedules may be used:

Gemcitabine may be administered IV at 1,000 mg/m$^2$ IV over 30 minutes. For example, gemcitabine may be administered IV at 1,000 mg/m$^2$ IV over 30 minutes on Days 1, 8, and 15 of each 28-day cycle and TH-302 may be administered on Days 1, 8, and 15 of each 28-day cycle. In an other example, gemcitabine and TH-302 are administered once weekly for seven weeks followed by one week of no administration, followed by one or more 28-day cycles in which TH-302 and gemcitabine are administered on Days 1, 8, and 15 of each 28-day cycle.

Docetaxel may be administered IV at 75 mg/m$^2$ over 60 minutes. For example, docetaxel may be administered IV at 75 mg/m$^2$ over 60 minutes on Day 1 of each 21-day cycle and TH-302 may be administered on Days 1 and 8 of each 21-day cycle.

Pemetrexed may be administered IV at 500 mg/m$^2$ over 10 minutes. For example, pemetrexed may be administered IV at 500 mg/m$^2$ over 10 minutes on Day 1 of each 21-day cycle and TH-302 may be administered on Days 1 and 8 of each 21-day cycle.

Doxorubicin may administered as bolus injection at 75 mg/m$^2$ on Day 1 of a 21-day cycle and TH-302 may be administered on Days 1 and 8 of each 21-day cycle.

The following sections (A)-(E) provide additional discussion of treatment of cancers using TH-302 in combination with other anticancer agents. Although illustrative dosages and schedules are described below, it will be appreciated that for treatment of cancer, e.g., lung, prostate, pancreatic, colon, and soft tissue sarcomas, the dose and schedule of administration of TH-302 and other agents may include the doses and schedules described elsewhere in this description.

A. Treatment of Lung Cancer Using TH-302 in Combination Therapy with Docetaxel, Pemetrexed, a Platinum-Containing Drug, Doxorubicin, or Gemcitabine The present invention provides methods for treating subjects with NSCLC of squamous cell histology by administering TH-302 in combination with pemetrexed, docetaxel, gemcitabine, a platinum-containing drug, or doxorubicin.

As discussed in, e.g., Examples 4 and 5, infra, TH-302 may be administered to patients with lung cancer, including SCLC, NSCLC, and NSCLC of squamous cell histology in combination with other anticancer agents.

In clinical trials, analysis was carried out on ten human subjects with relapsed or refractory NSCLC who had been treated with the combination of TH-302 plus pemetrexed or TH-302 plus docetaxel. RECIST tumor assessments were performed for eight subjects. Three of eight subjects had partial responses while four of these same eight subjects had stable disease. The historical response rate in second-line NSCLC is less than 10% in several large pivotal studies. These eight subjects have received a median of 2.5 prior systemic chemotherapies. Two of the eight subjects continued on the study (e.g., receiving Cycle 5 to Cycle 16). Two of the three subjects with partial responses discontinued after completing the study in the absence of progression; one had completed 10 cycles and the other had received 16 cycles.

Two subjects with recurrent/refractory NSCLC were treated with gemcitabine and TH-302. One of the two subjects had a RECIST partial response and continued on-study (receiving Cycle 5).

Two of the partial responses described above, one in combination with docetaxel and one in combination with gemcitabine, were seen in subjects with NSCLC of squamous cell histology. NSCLC of squamous cell histology is particularly refractory to chemotherapy. The pemetrexed-approved indications in NSCLC exclude subjects with NSCLC of squamous cell histology. The one patient with NSCLC of squamous cell histology treated with pemetrexed in combination with TH-302 continued on-study at Cycle 5 with stable disease.

i) Docetaxel

The present invention provides a method of treating a patient diagnosed with lung cancer (e.g., NSCLC) comprising administering a therapeutically effective dose of TH-302 in combination with a therapeutically effective dose of docetaxel. As discussed in Example 4, infra, administration of TH-302 and docetaxel showed antitumor activity in human patients. As shown in Example 6, infra, administration of a single dose of TH-302 and a single dose of docetaxel inhibited tumor growth in an H460 ectopic lung cancer model. Also, in a series of ectopic lung cancer models, some using H460 cells and some using Calu-6 cells, administration of a series of doses of TH-302 and a variety of chemotherapeutic agents inhibited tumor growth. The tumor growth inhibition was greater than that with either TH-302 or other chemotherapy alone.

Therapeutically effective doses of docetaxel (e.g., Taxotere; Sanofi-Aventis) may be determined by medical professionals by reference to materials available from the FDA and/or the medical literature. An exemplary dose, for illustration and not limitation, is 75 mg/m$^2$ administered as a one-hour intravenous infusion. Illustrative therapeutically effective doses of TH-302 are described above. Other doses may be used as deemed appropriate by medical professionals and/or approved by the FDA.

In some embodiments, administration of docetaxel is preceded by administration of TH-302, with the gap between the end of TH-302 administration and the beginning of docetaxel administration being at least 30 minutes to one hour, typically at least 2 hours, and in any event no more than 24 hours. In some embodiments, the duration of the time between TH-302 and docetaxel administrations is from 1 to 10 hours, from 2 to 6 hours, or from 3 to 5 hours. In some embodiments the gap between the end of TH-302 administration and the beginning of docetaxel administration is about 2 hours.

ii) Pemetrexed

The present invention also provides a method for treating a patient diagnosed with lung cancer, including NSCLC, comprising administering a therapeutically effective dose of TH-302 in combination with administering a therapeutically effective dose of pemetrexed. As discussed in Example 4, infra, administration of TH-302 and pemetrexed showed antitumor activity in human patients. As discussed in Example 6, infra, administration of TH-302 and pemetrexed dramatically inhibited tumor growth in a NSCLC model.

Therapeutically effective doses of pemetrexed may be determined by medical professionals by reference to materials available from the FDA and/or the medical literature. An exemplary dose, for illustration and not limitation, is 500 mg/m$^2$ administered IV over 10 minutes once every three weeks. Illustrative therapeutically effective doses of TH-302 are described above. Other doses may be used as deemed appropriate by medical professionals and/or approved by the FDA.

In some embodiments, administration of pemetrexed is preceded by administration of TH-302, with the gap between the end of TH-302 administration and the beginning of pemetrexed administration being at least one hour and not more than 24 hours. In some embodiments, the duration of the time between TH-302 and pemetrexed administrations is from 1 to 10 hours, from 2 to 6 hours, or from 3 to 5 hours. In some embodiments the gap between the end of TH-302 administration and the beginning of pemetrexed administration is about 2 hours.

iii) Platinum-Containing Drugs

The present invention also provides a method for treating a patient diagnosed with lung cancer (including NSCLC) comprising administering a therapeutically effective dose of TH-302 in combination with administering a therapeutically effective dose of a platin (e.g., such as cisplatin or carboplatin). As discussed in Example 6, infra, administration of TH-302 and cisplatin inhibited tumor growth in two lung cancer models, one using H460 cells and one using Calu-6 cells. As discussed in Example 6, infra, administration of TH-302 and carboplatin inhibited tumor growth in an H460 lung cancer model.

Therapeutically effective doses of cisplatin and carboplatin may be determined by medical professionals by reference to materials available from the FDA and/or the medical literature. An exemplary dose of cisplatin, for illustration and not limitation, is 100 mg/m$^2$ once every four weeks. Therapeutically effective doses of carboplatin may be determined by medical professionals using the Calvert formula (Calvert et al., 1989, *J. Clin. Oncol.* 7:1748-56). Illustrative therapeutically effective doses of TH-302 are described above for illustration. Other doses may be used as deemed appropriate by medical professionals and/or approved by the FDA.

In some embodiments, administration of the platinum-containing drug is preceded by administration of TH-302, with the gap between the end of TH-302 administration and the beginning of platinum-containing drug administration being at least 30 minutes to one hour, typically at least 2 hours, and in any event no more than 24 hours. In some embodiments the duration of the time between TH-302 and platinum-containing drug administrations is from 1 to 10 hours, from 2 to 6 hours, or from 3 to 5 hours. In some embodiments the gap between the end of TH-302 administration and the beginning of administration of a platinum-containing drug is about 2 hours.

iv) Doxorubicin

The present invention also provides a method for treating a patient diagnosed with lung cancer comprising administering a therapeutically effective dose of TH-302 in combination with administering a therapeutically effective dose of doxorubicin. As discussed in Example 5, infra, administration of TH-302 and doxorubicin showed antitumor activity in human patients. As discussed in Example 6, infra, administration of TH-302 and doxorubicin inhibited tumor growth in a Calu-6 lung cancer model.

Therapeutically effective doses of doxorubicin may be determined by medical professionals by reference to materials available from the FDA and/or the medical literature. An exemplary dose is 40 to 75 mg/m$^2$ given as a single intravenous injection every 21 to 28 days. Therapeutically effective doses of TH-302 are described above. Other doses may be used as deemed appropriate by medical professionals and/or approved by the FDA.

In some embodiments, administration of doxorubicin is preceded by administration of TH-302, with the gap between the end of TH-302 administration and the beginning of doxorubicin administration being at least 30 minutes to one hour, typically at least 2 hours, and in any event no more than 24 hours. In some embodiments the duration of the time between TH-302 and doxorubicin administration is from 1 to 10 hours, from 2 to 6 hours, or from 3 to 5 hours. In some embodiments the gap between the end of TH-302 administration and the beginning of doxorubicin administration is about 2 hours.

v. Gemcitabine

The present invention also provides a method for treating a patient diagnosed with lung cancer comprising administering a therapeutically effective dose of TH-302 in combination with administering a therapeutically effective dose of gemcitabine. As discussed in Example 4, infra, administration of TH-302 and gemcitabine had beneficial effect in patients with, e.g., pancreatic cancer.

Therapeutically effective doses of gemcitabine may be determined by medical professionals by reference to materials available from the FDA and/or the medical literature. An exemplary dose is 1000 mg/m$^2$ given i.v. over 30 minutes on days 1, 8 and 15 of a 28 day cycle. Therapeutically effective doses of TH-302 are described above. Other doses may be used as deemed appropriate by medical professionals and/or approved by the FDA.

In some embodiments, administration of doxorubicin is preceded by administration of TH-302, with the gap between the end of TH-302 administration and the beginning of gemcitabine administration being at least 30 minutes to one hour, typically at least 2 hours, and in any event no more than 24 hours. In some embodiments the duration of the time between TH-302 and gemcitabine administrations is from 1 to 10 hours, from 2 to 6 hours, or from 3 to 5 hours. In some embodiments the gap between the end of TH-302 administration and the beginning of gemcitabine administration is about 2 hours.

B. Treatment of Prostate Cancer Using TH-302 in Combination Therapy with a Taxane The present invention provides a method for treating a patient diagnosed with prostate cancer comprising administering a therapeutically effective dose of TH-302 in combination with administering a therapeutically effective dose of a taxane such as docetaxel or paclitaxel. As discussed in Example 6, infra, administration of TH-302 and docetaxel or paclitaxel dramatically inhibited tumor growth in a prostate cancer model.

Therapeutically effective doses of taxanes may be determined by medical professionals by reference to materials available from the FDA and/or the medical literature. For illustration and not limitation, an exemplary dose is 75-100 mg/m$^2$ given as an intravenous infusion once every 21 days for docetaxel and 175 mg/m$^2$ given as an intravenous infusion every 21 days for paclitaxel. Illustrative therapeutically effective doses of TH-302 are described above. Other doses may be used as deemed appropriate by medical professionals and/or approved by the FDA.

Two human subjects with castrate resistant prostate cancer have been treated with the combination of TH-302 plus docetaxel. RECIST tumor assessments have been performed for both subjects and both subjects had stable disease. Both subjects had a decrease in PSA of over 50% from their baseline value. One of the two had severe pain involving the lumbar spine and this resolved on treatment. After 5 cycles, one of the two subjects had a >90% decrease in PSA dropping from 861 ng/ml to 45 ng/ml; the other subject has had a >50% decrease in PSA from the baseline PSA of 28 ng/ml.

In some embodiments, administration of paclitaxel or docetaxel is preceded by administration of TH-302, with the gap between the end of TH-302 administration and the beginning of paclitaxel or docetaxel administration being at least 30 minutes to one hour, typically at least 2 hours, and in any event no more than 24 hours. In some embodiments, the duration of the time between TH-302 and paclitaxel or docetaxel administrations is from 1 to 10 hours, from 2 to 6 hours, or from 3 to 5 hours. In some embodiments the gap between the end of TH-302 administration and the beginning of paclitaxel or docetaxel administration is about 2 hours.

C. Treatment of Pancreatic Cancer Using TH-302 in Combination Therapy with Gemcitabine The present invention provides a method for treating a patient diagnosed with pancreatic cancer comprising administering a therapeutically effective dose of TH-302 in combination with administering a therapeutically effective dose of gemcitabine. Administration of TH-302 and gemcitabine provided benefit to patients with first-line pancreatic cancer (see Example 4, infra). Moreover, administration of TH-302 and gemcitabine dramatically inhibited tumor growth in a pancreatic cancer model (see Example 6, infra). While the maximum tolerated dose for TH-302 in combination with gemcitabine has not been established, it is anticipated to be at least 340 mg/m2. This dose is effective for treating subjects with first-line pancreatic cancer.

Therapeutically effective doses of gemcitabine may be determined by medical professionals by reference to materials available from the FDA and/or the medical literature. An exemplary dose, for illustration and not limitation, is 1,000 mg/m$^2$ administered IV over 30 minutes once per week. Illustrative therapeutically effective doses of TH-302 are described above. Other doses may be used as deemed appropriate by medical professionals and/or approved by the FDA.

In some embodiments, administration of gemcitabine is preceded by administration of TH-302, with the gap between the end of TH-302 administration and the beginning of gemcitabine administration being at least 30 minutes to one hour, typically at least 2 hours, and in any event no more than 24 hours. In some embodiments, the duration of the time between TH-302 and gemcitabine administrations is from 1 to 10 hours, from 2 to 6 hours, or from 3 to 5 hours. In some embodiments the gap between the end of TH-302 administration and the beginning of gemcitabine administration is about 2 hours.

D. Treatment of Soft Tissue Sarcomas Using TH-302 in Combination Therapy with Doxorubicin The present invention provides a method for treating a patient diagnosed with a soft tissue sarcoma comprising administering a therapeutically effective dose of TH-302 in combination with administering a therapeutically effective dose of doxorubicin. Administration of TH-302 and doxorubicin provided benefit to patients with soft tissue sarcomas (see Example 5, infra). Moreover, administration of TH-302 and doxorubicin inhibited tumor growth in a sarcoma model (see Example 6, infra).

Therapeutically effective doses of doxorubicin may be determined by medical professionals by reference to materials available from the FDA and/or the medical literature. An exemplary dose; for illustration and not limitation, is 40 to 60 mg/m$^2$ given as a single intravenous injection every 21 to 28 days. Illustrative therapeutically effective doses of TH-302 are described above. The maximum tolerated dose for the TH-302 in combination with a doxorubicin regimen has not been established, but subjects can be treated, in accordance with the methods of the invention at a TH-302 dose of at least 240 mg/m$^2$ in combination with the approved doxorubicin dose of 75 mg/m$^2$. Other doses may be used as deemed appropriate by medical professionals and/or approved by the FDA.

In some embodiments, administration of doxorubicin is preceded by administration of TH-302, with the gap between the end of TH-302 administration and the beginning of doxorubicin administration being at least 30 minutes to one hour, typically at least 2 hours, and in any event no more than 24 hours. In some embodiments, the duration of the time between TH-302 and doxorubicin administration is from 1 to 10 hours, from 2 to 6 hours, or from 3 to 5 hours. In some embodiments the gap between the end of TH-302 administration and the beginning of doxorubicin administration is about 2 hours.

E. Treatment of Colon Cancer Using TH-302 in Combination Therapy with Cisplatin (CDDP) or 5-fluorouracil (5FU)

The present invention provides a method for treating a patient diagnosed with colon cancer comprising administering a therapeutically effective dose of TH-302 in combination with administering a therapeutically effective dose of cisplatin. As discussed in Example 6, infra, administration of TH-302 and cisplatin inhibited tumor growth in a HT-29 colon cancer model.

In one aspect, the invention provides a patient diagnosed with colon cancer comprising administering a therapeutically effective dose of TH-302 and administering a therapeutically effective dose of 5-fluorouracil (5FU). As discussed in Example 6, infra, administration of TH-302 and 5FU inhibited tumor growth in an HT-29 colon cancer model.

Therapeutically effective doses of cisplatin may be determined by medical professionals by reference to materials available from the FDA and/or the medical literature. An exemplary dose, for illustration and not limitation, is 100 mg/m$^2$ once every 3 to 4 weeks.

Therapeutically effective doses of 5FU may be determined by medical professionals by reference to materials available from the FDA and/or the medical literature. An exemplary dose, for illustration and not limitation, is 150 mg/m$^2$ daily.

Illustrative therapeutically effective doses of TH-302 are described above. Other doses may be used as deemed appropriate by medical professionals and/or approved by the FDA.

In some embodiments, administration of 5FU or CDDP is preceded by administration of TH-302, with the gap between the end of TH-302 administration and the beginning of 5FU or CDDP administration being at least 30 minutes to one hour, typically at least 2 hours, and in any event no more than 24 hours. In some embodiments, the duration of the time between TH-302 administration and administration of 5FU or CDDP is from 1 to 10 hours, from 2 to 6 hours, or from 3 to 5 hours. In some embodiments the gap between the end of TH-302 administration and the beginning of 5FU or CDDP administration is about 2 hours.

F. Combination Therapy with Other Compounds of Formula I

While the combination therapies described above have been described with respect to TH-302, the methods of the invention also include combination therapies with other compounds of Formula I, including, without limitation, TH-281. While the therapeutically effective dose may vary depending on which compound of Formula I is selected, the dose will typically be an amount in the range of about 200 mg/m$^2$-about 700 mg/m$^2$, about 300 mg/m$^2$-about 600 mg/m$^2$, about 350 mg/m$^2$-about 550 mg/m$^2$, about 400 mg/m$^2$-about 500 mg/m$^2$, about 400 mg/m$^2$-about 600 mg/m$^2$, and about 450 mg/m$^2$-about 550 mg/m$^2$. In various embodiments of the present invention, the dose administered is about 560 mg/m$^2$, 480 mg/m$^2$, 400 mg/m$^2$, 340 mg/m$^2$, 240 mg/m$^2$, or 120 mg/m$^2$. In other embodiments, the dose administered is in an amount in the range of about 700 mg/m$^2$-about 1200 mg/m$^2$ or about 800 mg/m$^2$-about 1000 mg/m$^2$.

EXAMPLES

The following examples are intended for illustration only and should not be construed to limit the scope of the invention. Example 1 describes formulations of the invention. Example 2 describes TH-302 monotherapy. Example 3 demonstrates the advantages of administering a HAP prior to administering another anti-cancer agent and incorporating a delay period between administrations. Examples 4 and 5 demonstrate the efficacy of TH-302 combination therapies in treating human cancers in human patients. In human trials lyophilized TH-302 was resuspended in D5W for administration to patients. Example 6 demonstrates the efficacy of TH-302 combination therapies in treating human cancers in animal models.

Example 1

Pharmaceutical Formulations of TH-302

This example describes pharmaceutical formulations of TH-302 as well as the results of experimentation demonstrating the advantages of certain formulations. As discussed below, a formulation containing TH-302, ethanol and TWEEN 80 provided advantages over other formulations including higher solubility of TH-302, allowing for a more concentrated solution, greater stability on storage, and the absence of precipitation when the concentrated formulation is diluted into D5W or saline.

The experimentation was performed on the following systems (or equivalents): HP 1090 Series II, with Alltech, Alltima C18, 50×4.6, 3 μM or 5 μm HPLC column; HP1090 pump; Diode-Array Detector; and Chemstation version A.08.01 data acquisition system. The following reversed phase HPLC conditions were used for the experimental studies: column temperature was room temperature; there was no sample thermostat; the detector wavelength was 325 nm, 254 nm; the pump configuration was gradient; the flow rate was 0.8 ml/min.; the injection volume was 10 μL; the run time was 11 min.; the needle wash was with ethyl alcohol; the diluent and blank were water. The Gradient Table was as follows:

TABLE 4

| Time (mins) | Mobile phase A (%) (water) | Mobile phase B (%) (acetonitrile) |
|---|---|---|
| 0.01 | 95 | 5 |
| 4.5 | 5 | 95 |
| 7 | 5 | 95 |
| 8 | 95 | 5 |
| 11 | 95 | 5 |

The materials and reagents were TH-302, prepared under GMP by Syngene; anhydrous 200 proof Sigma-Aldrich Cat. No. 459836-2L ethyl alcohol; HPLC grade or equivalent acetonitrile and water; benzyl alcohol Sigma-Aldrich Cat. No. 108006-100 ml; N,N-dimethylacetamide (DMA) Sigma-Aldrich Cat. No. 185884-500 ml; and 2 ml Vial Labfile AMB Wheaton Cat. No. W224681.

TH-302 formulations were subjected to different conditions to produce partial degradation. The test solutions and standards were individually stressed under the same conditions. Test solutions for evaluation were prepared according to the procedures described below.

A following series of comparative formulations (1, 2A and 2B) were prepared to evaluate the stability of TH-302 using various combinations of the indicated solvents (ethanol (EtOH) and in DMA/EtOH/Benzyl alcohol) without a non-ionic surfactant. These formulations were studied in accelerated stability conditions at various temperatures (4° C., 20° C., and 37° C.) for up to 154 days.

Formulation 1 was prepared as follows. A 50 mg/ml solution of TH-302 in EtOH was prepared. 2.5 g of TH-302 were weighed out and transferred into a volumetric flask (50 ml). 46 ml of EtOH were added and the mixture was stirred at room temperature for 1.5 hours. After all the solid disappeared completely, the solution was diluted to 50 ml by the addition of ethanol. The solution was transferred into 2-ml vials with 1 ml of solution in each vial. The concentration was 50 mg/ml. The vials were stored at different temperatures (4° C. (refrigerator); 20° C. (bench); 37° C. (water bath)) for the various times shown below. Samples were taken on days 28, 65, 106 and 154 for LC analysis. 50 µL was aliquoted from the 50 mg/ml TH 302 solutions, added to volumetric flasks (50 ml), and diluted with water to the 50 ml volume and mixed well. The concentration was 50 µg/ml.

The stability of Formulation 1 at the various temperatures and times is shown in the following Tables 5-7.

TABLE 5

Stability of TH-302 (50 mg/ml) in EtOH at 37° C.

| | Relative retention time to TH-302 | | |
|---|---|---|---|
| Days | TH-302 | 0.98* | 0.96** |
| 0 | 97.64% | 2.36% | N/D |
| 28 | 95.66% | 2.34% | 2.00% |
| 65 | 92.54% | 2.37% | 5.09% |

TABLE 6

Stability of TH-302 (50 mg/ml) in EtOH at 20° C.

| | Relative retention time to TH-302 | | |
|---|---|---|---|
| Days | TH-302 | 0.98* | 0.96 |
| 0 | 97.64% | 2.36% | N/D |
| 28 | 97.65% | 2.35% | N/D |

TABLE 6-continued

Stability of TH-302 (50 mg/ml) in EtOH at 20° C.

| | Relative retention time to TH-302 | | |
|---|---|---|---|
| Days | TH-302 | 0.98* | 0.96 |
| 65 | 97.61% | 2.39% | N/D |
| 106 | 97.66% | 2.34% | _** |
| 154 | 97.0% | 2.44% | 0.56% |

TABLE 7

Stability of TH-302 (50 mg/ml) in EtOH at 4° C.

| | Relative retention time to TH-302 | | |
|---|---|---|---|
| Days | TH-302 | 0.98* | 0.96** |
| 0 | 97.64% | 2.36% | N/D |
| 154 | 97.51% | 2.49% | N/D |

*Mono chloro impurity
**Unidentified degradation product was observed,
_ Product couldn't be integrated.
N/D not detected HPLC chromatograms of TH-302 (50 mg/ml) in EtOH at 37° C. for 65 days and of TH-302 in EtOH (50 mg/ml) at 4° C. for 154 days showed that TH-302 in ethanol (50 mg/ml) is stable at 4° C., and shows no degradation out to day 154. However, TH-302 in this formulation shows degradation when stored at higher temperatures, e.g. 37° C. While TH-302 in pure ethanol is relatively stable at low temperatures, the highest solubility of TH-302 in ethanol is about 80 mg/ml even at higher temperatures.

A degradation product having the structure below [(2-chloroethyl)({[(2-bromoethyl)amino][(2-nitro-3-methylimidazol-4-yl)methoxy]phosphoryl})amine] ("monochloro impurity") (2.4%) was noted at study start and did not notably increase over time at any of the stability condition temperatures tested.

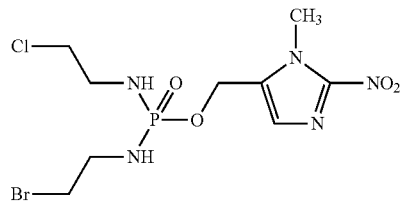 [SMILES: Cn1c(COP(=O)(NCCCl)NCCBr)cnc1[N+](=O)[O-]]

Formulation 2A was prepared as follows. 1.2 g of TH-302 was weighed out and transferred into a solution of benzyl alcohol (600 mg) and DMA (1200 mg) in a volumetric flask (10 ml). The mixture became a clear solution after agitating for 5 min. The solution was diluted to 10 ml by the addition of ethanol. The solution was transferred into 2 ml vials with 0.2 ml solution in each vial. The TH-302 concentration was 120 mg/ml. The vials were stored at different temperatures (4° C. (refrigerator); 20° C. (bench); 37° C. (water bath)) for the various times shown below.

Formulation 2A that was at 4° C. was warmed to room temperature (RT) and kept at this temperature for 30 min. Formulation 2A at 37° C. was cooled down to RT kept at this temperature for 30 min. 20 µL of the 120 mg/ml TH 302 solutions from each vial stored at different temperatures (4° C.; 20° C.; 37° C.) was transferred into a corresponding volumetric flask (50 ml). The solutions were then diluted with water to the 50 ml volume and mixed well. The final concentration of TH-302 was 48 µg/ml. Formulation 2B was prepared using the same procedure as for preparing solution 2A, except the amount of DMA was reduced to 1000 mg.

The stability of Formulations 2A and 2B at various temperatures and times is shown in the following tables.

TABLE 8

Stability of TH-302 in DMA/EtOH/Benzyl alcohol (120 mg/ml) at 37° C. Formulation 2A

| | Relative retention time to TH-302 | | |
|---|---|---|---|
| Days | TH-302 | 0.98* | 0.96** | 0.95** |
| 0 | 97.36% | 2.64% | 0 | 0 |
| 28 | 94.12% | 2.60% | 2.30% | 0.98% |

TABLE 9

Stability of TH-302 in DMA/EtOH/Benzyl alcohol (120 mg/ml) at 37° C. Formulation 2B

| | Relative retention time to TH-302 | | |
|---|---|---|---|
| Days | TH-302 | 0.98* | 0.96** | 0.95** |
| 0 | 97.70% | 2.29% | 0 | 0 |
| 28 | 94.41% | 2.56% | 2.20% | 0.83% |

*Mono chloride impurity;
**Other Degradation product

TABLE 10

Stability of TH-302 in DMA/EtOH/Benzyl alcohol (120 mg/ml) at 20° C. Formulation 2A

| | Relative retention time to TH-302 | |
|---|---|---|
| Days | TH-302 | 0.98* | 0.96** |
| 31 | 97.45% | 2.55% | 0 |
| 67 | 97.27% | 2.48% | 0.28% |

TABLE 11

Stability of TH-302 in DMA/EtOH/Benzyl alcohol (120 mg/ml) at 20° C. Formulation 2B

| | Relative retention time to TH-302 | |
|---|---|---|
| Days | TH-302 | 0.98* | 0.96** |
| 31 | 97.65% | 2.35% | 0 |
| 67 | 97.24% | 2.52% | 0.25% |

*Mono chloride impurity;
**New impurity

TABLE 12

Stability of TH-302 (120 mg/ml) in DMA/EtOH/Benzyl alcohol at 4° C. Formulation 2A

| | Relative retention time to TH-302 | |
|---|---|---|
| Days | TH-302 | 0.98* | 0.96 |
| 31 | 97.57% | 2.43% | 0 |
| 67 | 97.57% | 2.43% | 0 |

TABLE 13

Stability of TH-302 (120 mg/ml) in DMA/EtOH/Benzyl alcohol at 4° C. Formulation 2B

| | Relative retention time to TH-302 | |
|---|---|---|
| Days | TH-302 | 0.98* | 0.96 |
| 31 | 97.54% | 2.46% | 0 |
| 67 | 97.60% | 2.40% | 0 |

*Mono chloride impurity

HPLC analysis of the samples showed that TH-302 is stable in DMA/EtOH/Benzyl alcohol (120 mg/ml) at 4° C. and room temperature (RT) for at least 10 weeks (67 days). Crystals of TH-302 were observed in 4° C. samples and dissolved upon warming to RT for 30 min. Two impurities (for a total of about 3%) were observed after TH-302 was incubated at 37° C. for 4 weeks in DMA/EtOH/Benzyl alcohol. One of the impurities (0.25%) was observed at RT after 10 weeks. The other impurity was the monochloro compound, which was present at time zero and did not notably increase. No difference between formulations 2A and 2B was observed. The comparison of Formulations 1, 2a and 2b showed that TH-302 is has similar stability in EtOH and in DMA/EtOH/Benzyl alcohol.

This study evaluated the stability of a 200 mg/ml TH-302 solution in PEG 400 without a nonionic surfactant (Formulation 3) for 4 weeks at 37° C. Formulation 3 was made with 2 g of TH-302, which was transferred into PEG-400 (10 ml). The mixture became a clear solution after agitating at 40° C. for 15 min. The solution was transferred into 2 ml vials with 0.2 ml solution in each vial. The concentration of TH-302 was 200 mg/ml. The vials were stored at different temperatures (2-8° C. (refrigerator, i.e., 4° C.); 37° C. (water bath)) for the various times shown below. This stock solution was cooled down to RT and kept at this temperature for 30 min. 20 µL of the 200 mg/ml TH 302 solutions were transferred into a volumetric flask (50 ml). The solutions were then diluted with water to the 50 ml volume and mixed well. The final concentration of TH-302 was 80 µg/ml. 19 ml of water was injected into this solution in a 100 ml vial and a dark brown clear solution was obtained. 50 µL of the resulting solution was transferred into a volumetric flask (5 ml) and diluted with water to 5 ml. The final concentration of TH-302 was 50 µg/ml. HPLC analysis showed that Formulation 3 was less stable than Formulations 1, 2A and 2B. The concentration of TH-302 in this formulation decreased over one month at room temperature, demonstrating this formulation did not keep TH-302 in solution (i.e., precipitation occurred).

Another comparative of Formulation 4, an aqueous solution of lyophilized TH-302 without a nonionic surfactant was conducted. The following procedure was used to prepare Formulation 4. 19 ml of water were injected into the TH-302 in a 100 ml vial and a dark brown clear solution was obtained. 50 µL of the resulting solution was transferred into a volumetric flask (5 ml) and diluted with water to 5 ml. The final concentration of TH-302 was 50 µg/ml. One formulation of TH-302 that has been used in human clinical trials is a lyophilized powder that is stored at −20° C. and reconstituted just prior to patient administration (reconstituted lyophilized product).

HPLC analysis was used to analyze the relative stability of Formulations 1-4 at 37° C. after 28 days. The results are shown in the following table.

TABLE 14

Stability of TH-302 in different formulations at 37° C. on Day 28

| Formulation | EtOH | EtOH/DMA | PEG-400 | Lyophilized TH-302 reconstituted in D5W |
|---|---|---|---|---|
| TH-302% | 95.6 | 94.4 | 84.2 | <1% |

Based on the stability data at 37° C. on day 28, TH-302 has the following stability order in the various formulations: Ethanol>Ethanol/Benzyl alcohol/DMA>PEG-400>>reconstituted lyophilized product.

Formulations of TH-302 in pure DMA proved to be problematic when the drug solution was reconstituted in saline or D5W. TH-302 precipitated out when the TH-302/DMA solution was reconstituted in saline or D5W bags at the final concentration of 5 mg/ml.

Formulations of TH-302 in DMA/PEG-400 proved to be problematic when the drug solution was reconstituted in saline or D5W. TH-302 precipitated out when the TH-302/DMA/PEG-400 solution was reconstituted in saline or D5W bags at the final concentration of 5 mg/ml.

A comparative study of Formulations 7A-L (TH-302 in EtOH/DMA/TWEEN 80 or EtOH/DMA) after reconstitution in saline was conducted as follows. First, the following vehicles were prepared.

Vehicle A was prepared as follows: Into a 20 ml vial was added a mixture of EtOH (4 ml), DMA (0.75 ml) and TWEEN 80 (0.25 ml). The mixture was then well mixed by stirring for 5 min.

Vehicle B was prepared as follows: Into a 20 ml vial was added a mixture of EtOH (3.75 ml), DMA (1.0 ml) and TWEEN 80 (0.25 ml). The mixture was then well mixed by stirring for 5 min.

Vehicle C was prepared as follows: Into a 20 ml vial was added a mixture of EtOH (3.5 ml), DMA (1.25 ml) and TWEEN 80 (0.25 ml). The mixture was then well mixed by stirring for 5 min.

Vehicle D was prepared as follows: Into a 20 ml vial was added a mixture of EtOH (4.25 ml), DMA (0.25 ml). The mixture was then well mixed by stirring for 5 min.

The following stock solutions of TH-302 were prepared from the above vehicles:

100 mg/ml solutions were prepared as follows: 50 mg of TH-302 was allowed to dissolve in 0.5 ml of vehicle A, B, C, D in a corresponding 2 ml vial. The mixture in each vial was stirred for 5 min and a clear solution was obtained from all the vehicles.

150 mg/ml solutions were prepared as follows: 75 mg of TH-302 was allowed to dissolve in 0.5 ml of vehicle A, B, C, D in a corresponding 2 ml vial. The mixture in each vial was stirred for 5 min and a clear solution was obtained from all the vehicles.

200 mg/ml solutions were prepared as follows: 100 mg of TH-302 was allowed to dissolve in 0.5 ml of vehicle A, B, C, D in a corresponding 2 ml vial. The mixture in each vial was stirred for 10 min and a clear solution was obtained from all the vehicles.

The stability of the various formulations of TH-302 stored at −20° C. was analyzed. 0.1 ml of each solution prepared by the method described above was transferred into the corresponding 2 ml vial, the solutions were stored at −20° C. for 24 hr, and precipitation of TH-302 from the solution was observed in some vehicle. The vials with TH-302 precipitation were moved to room temperature and allowed to stay at room temperature for 30 min to determine if TH-302 can redissolve into the solutions under these conditions. The results are shown in the following table.

TABLE 15

Stability of the solutions at −20° C. and redissolution of TH-302 into vehicle at room temperature

| Formulation | Vehicle | Concentration | Precipitation | Re-dissolution |
|---|---|---|---|---|
| 7A | A | 100 mg/ml | No | |
| 7B | A | 150 mg/ml | Yes | Yes |
| 7C | A | 200 mg/ml | Yes | No |
| 7D | B | 100 mg/ml | No | |
| 7E | B | 150 mg/ml | No | |
| 7F | B | 200 mg/ml | Yes | Yes |
| 7G | C | 100 mg/ml | No | |
| 7H | C | 150 mg/ml | No | |
| 7I | C | 200 mg/ml | No | |
| 7J | D | 100 mg/ml | No | |
| 7K | D | 150 mg/ml | Yes | Yes |
| 7L | D | 200 mg/ml | Yes | No |

The 150 mg/ml solutions from each vehicle were chosen to test the reconstitution in saline. 0.1 ml of the solution was re-dissolved in 3 ml of saline in the corresponding 20 ml flask. After the solutions were mixed completely, precipitation of TH-302 was observed in some tests. The test was repeated 4 times. Precipitation was not observed with vehicles A, B, and C (containing TWEEN 80), but was observed in one of the four tests of vehicle D (not containing TWEEN 80). Reconstitution of the formulated TH-302 solution in saline at 5 mg/ml showed that the addition of TWEEN 80 prevents the precipitation of TH-302. In addition, ethanol/DMA was a better solvent than ethanol or PEG-400 at higher concentrations of TH-302.

A comparative study of Formulations 8A-F (TH-302 in EtOH/DMA/TWEEN 80) after reconstitution of the solutions in saline was conducted. The stability of each TH-302 solution at −20° C. and 2-8° C. was tested. Three vials from each formulation were stored at 2-8° C. in the dark to test the stability of the solution. Analysis was performed on Days 0, 7, 18 and 31. TH-302 did not precipitate out from any of the six formulations at 2-8° C. over 31 days. When the solutions were stored at −20° C., half of the formulations gave TH-302 crystals over 24 hrs, but the crystals re-dissolved in less than 1 hr after the solutions were warmed to room temperature. The results are summarized in the following table (measured at Day 7).

TABLE 16

Stability of TH-302 solution at −20° C. and 2-8° C.

| Formulation | TH-302 (mg/ml) | % TWEEN 80 | % DMA | Precipitation at −20° C. | Redissolve at RT | Precipitation at 2-8° C. |
|---|---|---|---|---|---|---|
| 8A | 100 | 5 | 15 | Yes | Yes | No |
| 8B | 100 | 10 | 15 | No | | No |
| 8C | 150 | 5 | 15 | Yes | Yes | No |
| 8D | 150 | 10 | 15 | Yes | Yes | No |
| 8E | 150 | 5 | 20 | No | | No |
| 8F | 150 | 10 | 20 | No | | No |

The chemical stability of TH-302 in different formulations was also tested at different temperatures, and the results are summarized in the following tables.

TABLE 17

Chemical stability of TH-302 at 40° C.

| Formulation | Day 0 | Day 7 40° C. | Day 18 40° C. | Day 31 40° C. |
|---|---|---|---|---|
| 8A | 86.0 ± 0.7 | | 76.3 ± 6.5 | 65.1 ± 5.5 |
| 8B | 84.0 ± 1.2 | | 71.2 ± 8.1 | 63.9 ± 1.1 |
| 8C | 88.1 ± 4.5 | | 72.9 ± 6.4 | 70.3 ± 8.7 |
| 8D | 91.3 ± 2.6 | | 66.0 ± 3.4 | 63.6 ± 1.1 |
| 8E | 86.6 ± 1.6 | | 68.5 ± 7.1 | 73.6 ± 7.1 |
| 8F | 88.5 ± 1.7 | | 74.6 ± 7.7 | 67.8 ± 0.5 |
| DP | 88.2 ± 1.9 | 64.4 ± 3.1 | 52.9 ± 2.5 | 33.2 ± 0.4 |

TABLE 18

Chemical stability of TH-302 at 25° C.

| Formulation | Day 0 | Day 18 25° C. | Day 31 25° C. |
|---|---|---|---|
| 8A | 86.0 ± 0.7 | 81.8 ± 9.3 | 84.8 ± 8.5 |
| 8B | 84.0 ± 1.2 | 84.9 ± 3.7 | 86.4 ± 4.6 |
| 8C | 88.1 ± 4.5 | 84.6 ± 4.2 | 86.6 ± 2.0 |
| 8D | 91.3 ± 2.6 | 85.6 ± 5.1 | 79.7 ± 1.9 |
| 8E | 86.6 ± 1.6 | 83.8 ± 3.9 | 79.0 ± 2.9 |
| 8F | 88.5 ± 1.7 | 86.7 ± 3.6 | 74.3 ± 4.9 |
| DP | 88.2 ± 1.9 | 77.5 ± 6.7 | 70.2 ± 4.8 |

The above data show that TH-302 in the six formulations is significantly more stable than in the reconstituted lyophilized drug product formulation (DP; lyophilized TH-302 reconstituted in D5W), when the solutions were stored at 25° C. Three out of the 6 formulations showed only minimum degradation of TH-302 over 31 days when compared with TH-302 in the DP formulation under the similar conditions, which showed over 18% degradation. As the data above demonstrates, the use of TWEEN 80 allowed for a more concentrated formulation of TH-302 and was shown to stabilize TH-302 better than the other formulations at similar concentrations.

Accordingly, the combinations of ethanol, and TWEEN 80, or ethanol, TWEEN 80, and DMA are excellent formulations for TH-302. TH-302 has good solubility in these formulations (up to 300 mg/ml) depending on the ratio of DMA/Ethanol/TWEEN 80. While increasing the concentration of DMA in the vehicle enhances the solubility of TH-302 in the liquid formulation, may affect the chemical stability of TH-302 in the formulation. TWEEN 80 prevented TH-302 precipitation when the drug solution was reconstituted in saline or D5W. Based on these results, a combination of nonionic surfactant, ethanol, and optionally DMA provides a concentrated formulation of TH-302 with suitable stability for long-term storage.

Example 2

Treatment of Lung Cancer and Melanoma in Human Patients Using TH-302 Monotherapy A Phase 1 clinical trial was conducted with TH-302. The starting dose was 7.5 mg/m$^2$ IV over 30-60 min administered once weekly for 3 weeks of a 4 week cycle. A modified accelerated titration design was used. Two of five patients dosed at 670 mg/m$^2$ exhibited dose limiting toxicity (DLT): herpes simplex perianal/rectal ulcers and dehydration due to mucositis. Six patients were enrolled at an intermediate dose of 575 mg/m$^2$, and this dose was established as the MTD for this administration schedule, as five of the six patients did not exhibit a DLT at this dose.

There was evidence of anticancer activity even at the lowest dose, with one NSCLC patient exhibiting stable disease (SD) for 7.3 months. Two patients, one with SCLC treated at 480 mg/m$^2$ and another with melanoma treated at 670 mg/m$^2$, had unconfirmed partial responses, as described in more detail below; 16 patients had stable disease.

Mucosal toxicity was dose-limiting, and skin and mucosal toxicity was common at doses above 240 mg/m$^2$, but these were reversible. In one embodiment of the invention, TH-302 is co-administered with an agent that prevents or ameliorates skin and/or mucosal toxicity. The most common TH-302-related adverse events (AEs) were nausea, skin toxicity, vomiting and fatigue. Hematologic toxicity was mild and limited.

Treatment of Lung Cancer

In this study, a 39 year old male suffering from a lung cancer (a refractory small cell lung cancer) that had metastasized to liver was treated as follows. Lyophilized TH-302 was diluted with D5W and administered to the patient at an amount of 480 mg/m$^2$, according to the following 4 week dosing cycle: TH-302 was administered once every week for 3 weeks, on days 1, 8, and 15, followed by a week of no TH-302 administration. The patient was administered 2 cycles (i.e. 6 doses) of TH-302, and the lung and liver cancers assessed by a computed tomography (or CT) scan. The CT scan demonstrated that the cancer in lung and liver had reduced in area by over 50% (44% decrease in sum of the longest diameters [SLD] of target lesions). LDH had decreased 72%, and liver function tests had normalized. The Cycle 2 tumor assessment also showed a large empyema that required surgical intervention, and a 22-day delay of Cycle 3 dosing. Confirmation CT scan one month after the Cycle 2 scan showed progressive disease.

Three other patients with lung cancer (one with NSCLC and 2 with SCLC) in the study responded to TH-302 monotherapy with stable disease.

These results demonstrate that the methods of the invention are efficacious in the treatment of lung cancer, including NSCLC and SCLC.

Treatment of Melanoma

This study also demonstrated that the methods of the invention are useful in the treatment of melanoma. A 74 year old male patient suffering from a primary melanoma (a skin cancer) that had metastasized to liver and lung was treated as follows. TH-302 was administered to the patient at an amount of 670 mg/m$^2$ using a 4 week (28 day) dosing cycle: TH-302 was administered once every week for 3 weeks, on days 1, 8, and 15, followed by a week of no TH-302 administration. The patient was administered 2 cycles of TH-302 and assessed by a CT scan. The CT scan demonstrated that the cancer in lung and liver had reduced in area by over 50% (53% decrease in SLD of target lesions).

Enrollment in the study was expanded at the MTD in patients with metastatic melanoma. TH-302 was administered intravenously over 30-60 minutes on Days 1, 8 and 15 of a 28-day cycle. Eligible patients had ECOG≤1, at least one target lesion by RECIST, and acceptable hematologic, liver, and renal function. Patients with symptomatic brain metastases were excluded unless previously treated and well controlled for at least 3 months. Nine patients with metastatic melanoma have been treated in the study. The median age was 70 (range 23-78) with 5 females and 4 males and ECOG 0/1 in 4/5 patients. Four patients had an elevated baseline LDH. Metastatic sites included liver in 7 patients and lung in 6 patients. All patients had received at least one prior systemic chemotherapeutic regimen. Two serious adverse events, seizures and ascites, were reported; neither was considered related to study drug. Skin adverse events were reported in 8 patients and mucosal adverse events were reported in 4 patients including one grade 3 event. Myelosuppression was not significant, with one event of grade 3/4 neutropenia and anemia and no events of grade 3/4 thrombocytopenia. Eight patients have had RECIST tumor assessments. Three of 8 (37%) patients had RECIST partial responses (one confirmed, one unconfirmed, one unconfirmed continuing on study), 3 of 8 (38%) patients had ongoing stable disease after 2 months of therapy, and 2 of 8 (25%) patients had progressive disease.

Example 3

Effect of Administration Schedule for HAP and Non-HAP Chemotherapeutic Agents in Combination Therapy As demonstrated herein (also see Examples 4 and 5 below), combination therapy of cancer with HAP and non-HAP anticancer agents provide more efficacious treatment with fewer side effects. For this demonstration, ectopic models were employed in nude mice. Anti-tumor activity was evaluated by tumor growth delay (TGD) and tumor growth inhibition (TGI). Body weight change, gross and microscopic assessment of tissue changes, and hematologic assays served for toxicity assessment. Testing in these models was conducted generally as follows. $1 \times 10^6$ (H460 human non-small cell lung cancer or HT1080 human fibrosarcoma cells) or $3 \times 10^6$ (PC-3 human prostate cancer cells) were implanted in the subcutaneous space of the right flank to obtain ectopic xenograft models. Randomization and dosing was initiated when tumors reached a certain size (100-150 mm$^3$). API grade of TH-302 was used in all experiments while docetaxel, gemcitabine, cisplatin, pemetrexed, and doxorubicin were purchased from commercial sources.

In one study, the effect of different TH-302/docetaxel dosing regimens in the H460 tumor growth (NSCLC) model was examined. The H460 cells were prepared in 30% Matrigel and 70%. RPMI1640. Mice were anesthetized by isoflurane and were implanted subcutaneously with $1 \times 10^6$ cells (in 200 µl) at the flank position. We selected 110 mice bearing similar size tumors (~100 mm$^3$) for the study. Mice bearing similar tumor size were randomly assigned into different groups. Treatment started on day 1 (7 days after tumor implantation) except as noted. TH-302 was administered intraperitoneally (IP) at 150 mg/kg, and docetaxel was administered intravenously (IV) at 10 mg/kg. Animals were observed daily and tumor measurements and body weights recorded twice weekly. The tumor growth delay (TGD) to reach 500 mm$^3$ and 1000 mm$^3$ of drug treated tumors as compared to vehicle treated tumors and the tumor growth inhibition (TGI) (1-T/C) where T/C=(Tn−Ti)/(Cn−Ci) where Tn is tumor volume in the treatment group on Day n and Ti is the initial tumor volume in the treatment group, and Cn is the tumor volume in the vehicle control group on Day n and Ci is the initial tumor volume in the vehicle control group and Day n is the last measurement when the animals in the control group are all still alive are presented in Table 19. Different antitumor effects were observed with different dose sequencing. Results showed that, in general, TH-302 given before docetaxel produced a superior antitumor response, and administration of TH-302 4 hours before the chemotherapeutic was better than the other time intervals tested, e.g. 24 or 48 hours before, or simultaneously.

In a study conducted substantially as described above except the cells implanted were PC-3 human prostate cancer cells and $3 \times 10^6$ cells were implanted and mice were randomized into separate groups when their tumors reached ~150 mm$^3$ TH-302 first provided the best results. Administering the non-HAP drug (docetaxel) 4 hours after stopping the administration of the HAP drug (TH-302) demonstrated the best treatment efficacy. The results for the 2, 4, and 24 hour delay tests are included in Table 19, below.

In a study conducted substantially as described above except the cells implanted were H460 NSCLC cells and $1 \times 10^6$ cells were implanted and mice were randomized into separate groups when their tumors reached ~100 mm$^3$ and the chemotherapeutic employed was pemetrexed at a dose of 150 mg/kg given once a week (Q7D) for two weeks IP and the TH-302 was given at 100 mg/kg given once a week (Q7D) for two weeks IP. Administering the non-HAP drug (pemetrexed) 2 hours after the administration of the HAP drug (TH-302) demonstrated the best treatment efficacy, when compared to simultaneous administration or when a 4, 8, or 24 hour delay was employed. The results for the tests are included in Table 19.

In a study conducted substantially as described above except the cells implanted were HT1080 human fibrosarcoma cells and $1 \times 10^6$ cells were implanted and mice were randomized into separate groups when their tumors reached ~100 mm$^3$ and the chemotherapeutic employed was doxorubicin at a dose of 4 mg/k given once IV and the TH-302 was given at a dose of 100 mg/kg once. Administering the non-HAP drug (doxorubicin) drug 2 hours or 4 hours after the administration of the HAP drug (TH-302) demonstrated the best treatment efficacy, when compared to simultaneous administration or when an 8 or 24 hour delay was employed or when the doxorubicin was administered before the HAP drug with a 2 hour delay. The results for the tests are included in the Table below.

Simultaneous administration of the HAP and non-HAP anticancer agents exhibited the greatest toxicity. For example, co-incident administration of TH-302 and the chemotherapeutic often exhibited the most severe body weight (BW) loss when compared to the other schedules. This was observed in the PC-3 (prostate carcinoma) model in which TH-302 and docetaxel were administered and in the PC-3 prostate cancer model in which TH-302 and cisplatin were administered.

In a study conducted substantially as described above except the cells implanted were PC-3 human prostate cancer cells and $5 \times 10^6$ cells were implanted and mice were randomized into separate groups when their tumors reached ~100 mm$^3$ and the chemotherapeutic employed was cisplatin at a dose of 6 mg/k given once a week for 2 weeks (Q7D×2) IV and the TH-302 was given at a dose of 50 mg/kg once daily for 5 days a week for 2 weeks, and on the day both agents were given TH-302 was given 2 hours before, simultaneously, or 2 hours after the cisplatin. Administering the non-HAP drug (cisplatin) drug 2 hours after the administration of the HAP drug (TH-302) demonstrated the best treatment efficacy, when compared to contemporaneous administration or when the cisplatin was administered before the HAP drug with a 2 hour. TH-302 administered contemporaneously with docetaxol in the PC-3 prostate cancer model showed toxic side effects in the mice, and 6 out of 10 mice tested with this administration schedule were sacrificed due to >20% body weight loss.

Another test was conducted to demonstrate how combination treatment in accordance with present methods provides reduced toxicity, particularly with respect to suppression of blood cell counts. In this test, TH-302 was administered to CD1 mice, and gemcitabine was then administered 0, 2, 4, 8, 16, or 24 h after stopping the administration of TH-302. The safety of the combination administration was measured by its effect on in blood cell counts (white blood cells or WBC, neutrophil, lymphocytes, monocyte, red blood cells or RBC, and hemoglobin or Hb) 2 days after the administration of TH-302 (the higher the blood cell count, the safer being the administration of the drugs in combination). Both drugs were administered intraperitoneally; TH-302 was administered at a dose of 75 mg/kg, and gemcitabine was administered at 300 mg/kg. The results demonstrated that non-contemporaneous administration of TH-302 and gemcitabine, for example, when gemcitabine was administered 2 h or 4 h after the administration of TH-302, was less toxic than administering them together.

In summary, these experiments demonstrated that (i) the greatest antitumor efficacy was observed by a regiment in which the HAP anticancer agent was administered first, and there was some delay between administration of the HAP and administration of the non-HAP anticancer agent; and (ii) simultaneous administration of the HAP and non-HAP anticancer agents exhibited the greatest toxicity.

TABLE 19

| | Group | Days to 500 mm$^3$ | Days to 1000 mm$^3$ | TGD500, Days (vs. vehicle) | TGD1000, Days (vs. vehicle) | Ti | Tn | T/C | TGI |
|---|---|---|---|---|---|---|---|---|---|
| TH-302 + Docetaxel H460 NSCLC | Group 1: Vehicle | 13 | 20 | | | 97.35 | 1113.92 | | |
| | Group 2: TH-302 100 mg/kg ip once | 21 | 31 | 8 | 11 | 99.34 | 531.74 | 42.5% | 57.5% |
| | Group 3: Docetaxol 10 mg/kg iv once | 18 | 27 | 5 | 7 | 96.08 | 681.36 | 57.6% | 42.4% |
| | Group 4: TH-302 + Docetaxol (1 hr delay) | 21 | 32 | 8 | 12 | 96.49 | 525.00 | 42.2% | 57.8% |
| | Group 5: TH-302 + Docetaxol (4 hr delay) | 32 | >40 | 19 | >20 | 96.58 | 223.20 | 12.5% | 87.5% |
| | Group 6: TH-302 + Docetaxol (24 hr delay) | 25 | 34 | 12 | 14 | 97.32 | 373.24 | 27.1% | 72.9% |
| | Group 7: TH-302 + Docetaxol (48 hr delay) | 25 | 33 | 12 | 13 | 96.45 | 345.02 | 24.5% | 75.5% |
| | Group 8: Docetaxol + TH-302 (4 hr delay) | 25 | 35 | 12 | 15 | 97.37 | 400.38 | 29.8% | 70.2% |
| | Group 9: Docetaxol + TH-302 (24 hr delay) | 25 | 35 | 12 | 15 | 96.70 | 367.45 | 26.6% | 73.4% |
| | Group 10: Docetaxol + TH-302 (48 hr delay) | 22 | 31 | 9 | 11 | 97.79 | 506.61 | 40.2% | 59.8% |
| | Group 11: day 2 TH-302 + Docetaxol (1 hr delay) | 23 | 31 | 10 | 11 | 98.35 | 447.84 | 34.4% | 65.6% |
| TH-302 + Docetaxel PC-3 prostate cancer | Group 1: Vehicle | 16 | nd | | | 137.86 | 1005.44 | | |
| | Group 2: TH-302 150 mg/kg, ip, once | 25 | nd | 9 | nd | 137.63 | 559.95 | 48.7% | 51.3% |
| | Group 3: Docetaxol 10 mg/kg, iv, once | 26 | nd | 10 | nd | 137.55 | 563.22 | 49.1% | 50.9% |
| | Group 4: TH-302 + Docetaxol (coincidently) | 31 | nd | 15 | nd | 137.21 | 433.40 | 34.1% | 65.9% |
| | Group 5: TH-302 + Docetaxol (2 hr delay) | 32 | nd | 16 | nd | 137.22 | 389.14 | 29.0% | 71.0% |
| | Group 6: TH-302 + Docetaxol (4 hr delay) | 40 | nd | 24 | nd | 137.56 | 240.49 | 11.9% | 88.1% |
| | Group 7: TH-302 + Docetaxol (24 hr delay) | 38 | nd | 22 | nd | 137.41 | 262.84 | 14.5% | 85.5% |
| | Group 8: Docetaxol + TH-302 (2 hr delay) | 31 | nd | 15 | nd | 136.91 | 401.78 | 30.5% | 69.5% |
| | Group 9: Docetaxol + TH-302 (4 hr delay) | 37 | nd | 21 | nd | 137.10 | 312.62 | 20.2% | 79.8% |
| | Group 10: Docetaxol + TH-302 (24 hr delay) | 35 | nd | 19 | nd | 137.52 | 341.89 | 23.6% | 76.4% |
| TH-302 + Pemetrexed H460 NSCLC | Group 1: Vehicle | 12 | 21 | | | 117.01 | 1086.98 | | |
| | Group 2: TH-302 100 mg/kg ipQ7Dx2 | 19 | 30 | 7 | 9 | 115.80 | 598.34 | 49.7% | 50.3% |
| | Group 3: PMX 150 mg/kg ip Q7Dx2 | 14 | 24 | 2 | 3 | 115.31 | 817.45 | 72.4% | 27.6% |
| | Group 4: TH-302 + PMX (0 hr delay) | 19 | 30 | 7 | 9 | 115.65 | 619.70 | 52.0% | 48.0% |
| | Group 5: TH-302 + PMX (2 hr delay) | 22 | 31 | 10 | 10 | 115.41 | 481.15 | 37.7% | 62.3% |
| | Group 6: TH-302 + PMX (4 hr delay) | 21 | 28 | 9 | 7 | 115.19 | 557.19 | 45.6% | 54.4% |
| | Group 7: TH-302 + PMX (8 hr delay) | 22 | 31 | 10 | 10 | 115.44 | 481.56 | 37.7% | 62.3% |
| | Group 8: TH-302 + PMX (24 hr delay) | 22 | 30 | 10 | 9 | 114.68 | 504.77 | 40.2% | 59.8% |
| TH-302 + Doxorubicin HT1080 sarcoma | Group 1: Vehicle | 12 | nd | | | 109.20 | 998.94 | | |
| | Group 2: TH-302 100 mg/kg ip 1/wkx2wks | 22 | nd | 10 | nd | 109.43 | 334.66 | 25.3% | 74.7% |
| | Group 3: Dox 4 mg/kg iv 1/wkx2wks | 24 | nd | 12 | nd | 109.61 | 154.79 | 5.1% | 94.9% |
| | Group 4: TH-302 + Dox (0 hr delay) | 29 | nd | 17 | nd | 109.96 | 95.76 | −1.6% | 101.6% |
| | Group 5: TH-302 + Dox (2 hr delay) | 33 | nd | 21 | nd | 109.49 | 52.36 | −6.4% | 106.4% |
| | Group 6: TH-302 + Dox (4 hr delay) | 33 | nd | 21 | nd | 109.63 | 58.27 | −5.8% | 105.8% |
| | Group 7: TH-302 + Dox (8 hr delay) | 26 | nd | 14 | nd | 109.40 | 114.27 | 0.5% | 99.5% |
| | Group 8: TH-302 + Dox (24 hr delay) | 24 | nd | 12 | nd | 109.42 | 195.24 | 9.6% | 90.4% |
| | Group 9: Dox + TH-302 (2 hr delay) | 27 | nd | 15 | nd | 109.05 | 87.31 | −2.4% | 102.4% |
| TH-302 + Cisplatin PC-3 prostate cancer | Group 1: Vehicle | 14 | nd | nd | nd | 90.72 | 1061.83 | | |
| | Group 2: CisPt Q7Dx2wk + TH-302 50 mg/kg QDx5/wkx2wk (2 hr delay) | 27 | nd | 13 | nd | 91.47 | 338.67 | 25.50% | 74.50% |
| | Group 3: TH-302 50 mg/kg QDx5/wkx2wk + CisPt Q7Dx2wk (0 hr delay) | 30 | nd | 16 | nd | 93.12 | 250.73 | 16.20% | 83.80% |
| | Group 4: TH-302 50 mg/kg QDx5/wkx2wk + CisPt Q7Dx2wk (2 hr delay) | 30 | nd | 16 | nd | 89.33 | 216.11 | 13.10% | 86.90% |

Example 4

Combination Therapy with TH-302 and Gemcitabine, Docetaxel, or Pemetrexed

This Example demonstrates the non-contemporaneous administration of an anticancer agent other than TH-302 in combination with TH-302 for the treatment of cancer. A Phase 1/2, 3-arm, multicenter, dose-escalation study was conducted using a classic dose escalation design to demonstrate the efficacy and determine the safety of TH-302 when administered in combination with gemcitabine, docetaxel, or pemetrexed. The initial dose of TH-302 was 240 mg/m$^2$. TH-302 was administered by intravenous (IV) infusion over 30 minutes on Days 1, 8, and 15 of a 28-day (4 week) cycle (Arm A) or Days 1 and 8 of a 21-day (3 week) cycle (Arms B & C) as noted below. Gemcitabine, docetaxel or pemetrexed was administered 2 h after the TH-302 infusion was completed. The starting doses of gemcitabine, docetaxel or pemetrexed remained fixed according to approved doses listed in their respective product labeling. The treatment regimen, dose, schedule and cycle length of these drugs were as follows Treatment Arm A: Gemcitabine was administered IV at 1,000 mg/m$^2$ IV over 30 minutes on Days 1, 8, and 15 of each 28-day cycle. TH-302 was administered as above on Days 1, 8, and 15 of each 28-day cycle.

Treatment Arm B: Docetaxel was administered IV at 75 mg/m$^2$ over 60 minutes on Day 1 of each 21-day cycle. TH-302 was administered as above on Days 1 and 8 of each 21-day cycle.

Treatment Arm C: Pemetrexed was administered IV at 500 mg/m$^2$ over 10 minutes on Day 1 of each 21-day cycle. TH-302 was administered as above on Days 1 and 8 of each 21-day cycle.

A. Study Drug Exposure and Determination of Dose Limiting Toxicity

The dose was initiated at 240 mg/m$^2$ and dose escalation was then continued with 40% increases from the previous dose level; however lower dose increases of 20-40% were also applicable based on treatment outcome. The dose of TH-302 was escalated in cohorts of 3-6 patients. If a subject experienced a dose limiting toxicity (DLT), 3 additional patients were enrolled at that dose level for a total of 6 patients in that cohort. If no additional DLTs were observed, dose escalation was resumed. However, if 2 or more of 6 patients within a cohort experience a DLT, that dose was considered to exceed the maximum tolerated dose (MTD). The MTD was then defined at the next lower dose level in which 6 patients were treated and less than 1 subject experienced a DLT. The maximum dose of TH-302 used was the single agent (TH-302 monotherapy) MTD or the highest dose tested in that study if the MTD was not reached.

CT scans were done every 2 cycles. The objectives of the study were to determine the MTD and DLT of TH-302 and to evaluate the safety, pharmacokinetics (PK) and preliminary efficacy of TH-302 in combination with gemcitabine (G), docetaxel (D), or pemetrexed (P) in advanced solid tumors. Seventy-two patients have been enrolled and have sufficient follow-up to be included in the dose escalation summary. Fifty patients were enrolled with sufficient tumor assessment follow-up. Patients were enrolled at 7 US sites from August 2008 to August 2009 and received study drug. Study drug exposure and DLTs are summarized below.

TABLE 20

TH-302 plus Gemcitabine

| Dose (mg/m$^2$) | No. of Patients | No. DLT Evaluable | DLTs (description) | Median Cycles (Range) | On-going |
|---|---|---|---|---|---|
| 240 | 7 | 6 | 1 (grade 3 ALT elevation) | 4 (1-11+) | 3 |
| 340 | 6 | 3 | 0 | 3 (2-7) | 3 |
| 480 | 6 | 5 | 2 (grade 4 thrombocytopenia; grade 3 pain/fatigue) | 4 (2-6+) | 5 |
| 575 | 7 | 6 | 2 (grade 4 thrombocytopenia; grade 3 esophagitis) | 2 (1-3+) | 6 |

TABLE 21

TH-302 plus Docetaxel

| Dose (mg/m$^2$) | No. of Patients | No. DLT Evaluable | DLTs (description) | Median Cycles (Range) | On-going |
|---|---|---|---|---|---|
| 240 | 7 | 7 | 1 (febrile neutropenia) | 4 (1-10+) | 1 |
| 340 | 6 | 5 | 0 | 2 (1-8+) | 4 |
| 480 | 7 | 6 | 2 (grade 4 neutropenia) | 3 (2-6+) | 6 |

TABLE 22

TH-302 plus Pemetrexed

| Dose (mg/m$^2$) | No. of Patients | No. DLT Evaluable | DLTs (description) | Median Cycles (Range) | On-going |
|---|---|---|---|---|---|
| 240 | 5 | 3 | 0 | 10 (2-16) | 1 |
| 340 | 5 | 5 | 0 | 2 (2-8+) | 3 |
| 480 | 9 | 6 | 1 (grade 3 oral candidiasis) | 2 (1-6+) | 3 |
| 575 | 7 | 5 | 1 (grade 3 oral mucositis/Gr 4 thromocytopenia) | 3 (1-4+) | 3 |

The results to date demonstrate that TH-302 can be administered safely in combination with full dose gemcitabine, docetaxel or pemetrexed but may increase the hematologic toxicity of these agents.

The MTD of TH-302 plus gemcitabine is anticipated to be 340-400 mg/m$^2$; the MTD of TH-302 plus docetaxel is 340 mg/m$^2$ and the MTD of TH-302 plus pemetrexed is 480 mg/m$^2$. The primary dose limiting toxicities have been hematologic. While the contribution of TH-302 to the hematologic toxicity is hard to determine when TH-302 is combined with a myelosuppressive chemotherapy, greater hematologic toxicity than would be expected with single agent chemotherapy is evident in the gemcitabine and pemetrexed arms. Skin and mucosal toxicity are common at doses above 240 mg/m$^2$. The mechanism is unknown but may be due to activation of TH-302 in areas of epithelium that are normally hypoxic. The addition of TH-302 to standard chemotherapies does not appear to enhance the toxicity in other body systems. Higher response rates than would be expected with single agent chemotherapy are evident.

B. Anti-Tumor Activity

Anti-tumor activity was observed in the majority of patients. Multiple responses in pancreatic cancer, NSCLC and transitional cell cancers have been reported (see Tables 2 and 3 in the Detailed Description of the Invention, above).

To date, 45 patients have been assessed for response. Of these 12 patients (27%) had a RECIST criteria partial response (PR), 22 patients (49%) achieved stable disease (SD) and 11 patients (24%) had progressive disease. The partial response included both confirmed and unconfirmed partial responses. In a confirmed partial response, partial response was maintained through a subsequent response assessment at least 28 days later, and in an unconfirmed partial response, the partial response was reported at one assessment but was not maintained in a subsequent response assessment.

i) Gemcitabine Arm

In the TH-302 plus gemcitabine arm, TH-302 was administered intravenously for 30 to 60 minutes on days 1, 8 and 15 of a 28 day cycle. Gemcitabine is dosed according to its package insert on days 1, 8 and 15 of a 28 day cycle. The TH-302 maximum tolerated dose (MTD) has not been established with the dose cohort currently being expanded at 340 mg/m$^2$. Two dose limiting toxicities were reported at each of two higher TH-302 doses levels. Fifteen patients have had tumor assessments, 6 of whom had a PR in the following cancers: pancreatic (2), ovarian, esophageal, squamous non-small cell lung cancer (NSCLC) and thyroid and 7 patients with SD.

Eight human subjects with pancreatic cancer have been treated with TH-302 in combination with gemcitabine. RECIST tumor assessments have been performed for four subjects. At their initial tumor assessment, two of four subjects had partial responses and the other two of the same four subjects had stable disease. The historical response rate for first-line pancreatic cancer is less than 10% in multiple large studies. Two of these four subjects continue on-study and are receiving Cycle 4 or Cycle 6. One of the subjects with a partial response discontinued with an infection; the other discontinued after a new lesion was detected. CA19-9 is a protein that has been identified as a tumor marker for a number of gastrointestinal cancers including pancreatic cancer. Generally, values of CA19-9 (IU/ml) are associated with the extent of tumor burden. Higher levels of CA19-9 are associated with poorer survival. In addition, CA 19-9 responses, defined as a greater than 50% decrease from the baseline CA19-9, have been shown to predict for a better prognosis. Two of the four subjects had an elevated CA19-9 prior to the combination therapy. Both of these subjects had CA19-9 responses with CA19-9 decreases of 78% and 98%.

ii) Docetaxel Arm

In the TH-302 plus docetaxel arm, TH-302 was administered intravenously on days 1 and 8 of a 21 day cycle. Docetaxel was dosed according to its package insert on day 1 of the 21 day cycle. The TH-302 MTD has been established at 340 mg/m$^2$ and the dose expansion has been initiated at this dose in patients with castrate resistant prostate cancer and in patients with second-line NSCLC. Eleven patients have had tumor assessments, 2 of whom achieved PRs in NSCLC and anal cancer and 6 patients with SD.

iii) Pemetrexed Arm

In the TH-302 plus pemetrexed arm, TH-302 was administered intravenously on days 1 and 8 of a 21 day cycle. Pemetrexed was dosed according to its package insert on Day 1 of the 21 day cycle. The TH-302 MTD has been established at 480 mg/m$^2$ and the dose expansion has been initiated at a TH-302 dose of 400 mg/m$^2$ in patients with second-line non-squamous NSCLC. Nineteen patients have had tumor assessments, 4 of whom achieved PRs in NSCLC (2) and transitional cell carcinoma (2) and 9 patients with SD.

Overall, 8 patients with relapsed or refractory NSCLC have been treated with TH-302 in combination with either docetaxel or pemetrexed and have been assessed for response. Of the 8 patients assessed, 3 patients achieved PRs, 4 patients achieved SD and 1 patient had PD. The median time on treatment for the 8 patients has been 5.3 months.

Example 5

Combination Therapy with TH-302 and Doxorubicin

A Phase 1/2, multicenter, dose-escalation study of patients with soft tissue sarcoma using a classic dose escalation design was conducted to demonstrate the efficacy and safety of TH-302 when administered in combination with doxorubicin in accordance with the present invention. The dose of TH-302 was escalated in cohorts of 3-6 subjects. The initial dose of TH-302 was 240 mg/m$^2$, a dose with no Cycle 1 grade 2 or greater toxicity (excluding fatigue, nausea, vomiting, alopecia, and diarrhea) in the single agent Phase 1 study. A Dose Level minus 1 was built into the study. Dose escalation continued with 40% increases from the previous dose level; however, lower dose increases of 20-39% could also be administered.

If a subject experienced a DLT, 3 additional subjects were enrolled at that dose level for a total of 6 subjects in that cohort. If no additional DLTs were observed, dose escalation resumed. However, if 2 or more of 6 subjects within a cohort experience a DLT, that dose will be considered to exceed the MTD. The MTD will then be defined at the next lower dose level whereby 6 subjects are treated and <1 subject experiences a DLT. The maximum dose of TH-302 is the single agent MTD or the highest dose tested in that study if the MTD was not reached. MTD is based on toxicities occurring during the first cycle. An additional 12 subjects will be enrolled at the MTD for the dose expansion portion of the study.

TH-302 was administered by IV infusion over 30-60 minutes on Days 1 and 8 of a 21 day cycle. The dose of doxorubicin remained fixed: 75 mg/m$^2$ administered by bolus injection starting on Day 1 of a 21-day cycle (if serum bilirubin is above the ULN but ≤1.5×ULN, the dose was reduced to 56 mg/m$^2$). Doxorubicin was administered starting two hours after completion of TH-302 infusion on Day 1 of each cycle.

Ten patients have been treated in this study with TH-302, 6 patients at 240 mg/m$^2$ and 4 patients at 340 mg/m$^2$. The patient age range was 19-85. The sarcomas treated included liposarcoma (3), leiomyosarcoma (3), synovial sarcoma (2) and pleomorphic (2). The first 3 patients at 240 mg/m$^2$ had G4 neutropenia at Day 15. Subsequent patients are receiving granulocyte-stimulating factor (GCSF) on Day 8 in accordance with the methods of the invention. A DLT of Grade 4 thrombocytopenia at Day 15 and a DLT of grade 3 infection occurred in two patients treated at 340 mg/m$^2$. Myelosuppression appears to be the DLT, with the effects partially obviated by use of GCSF. Thus, in one embodiment of the invention GCSF is co-administered with TH-302 to treat cancer.

RECIST tumor assessments have been performed for seven subjects. Three of seven subjects had partial responses and another three of these same seven subjects have had stable disease. The historical response rate in first-line soft tissue sarcoma is between 15% and 25%. Two of the seven subjects continue on-study and are receiving Cycle 4 or Cycle 11. All three subjects with partial responses continued on-study to receive TH-302 alone after completing the doxorubicin component of the study.

Example 6

Combination Therapies with TH-302 in Cancer Models

This example demonstrates that the methods of the invention for combination therapy of cancer with HAP and non-HAP anticancer agents have anticancer activity superior to either agent by itself. For this demonstration, ectopic, orthotopic and metastatic models were employed in nude mice. Anti-tumor activity was evaluated by tumor growth inhibition (TGI) and tumor growth delay (TGD). Body weight change, gross and microscopic assessment of tissue changes, and hematologic assays served for toxicity assessment.

a) Methods

Testing in these models was conducted generally as follows. 1×10$^6$ H460 human non-small cell lung cancer or HT1080 human fibrosarcoma cells were implanted in the subcutaneous space of the right flank to obtain ectopic xenograft models. For the orthotopic pancreatic model, red-fluorescent protein (RFP) expressing MIA PaCa2 tumors were surgically implanted on the surface of the pancreas. The prostate metastatic model was created by the intraventricular injection of 3×10$^6$ luciferase-expressing PC-3 cells. Randomization and dosing was initiated when tumors reached a certain size (100-150 mm$^3$) in ectopic models, or imaging showed certain disease progression in the orthotopic and metastatic models. API grade of TH-302 was used in all experiments while docetaxel, gemcitabine, doxorubicin and pemetrexed were purchased from commercial sources.

b) TH-302 with Pemetrexed in a Lung Cancer Model

Inhibition of tumor growth after administration of the combination of TH-302 and pemetrexed was greater than for either drug individually in an ectopic lung cancer model using H460 cells. See Table 23.

c) TH-302 with Doxorubicin in a Lung Cancer Model

Inhibition of tumor growth after administration of TH-302 and doxorubicin drugs was greater than for either drug individually in an ectopic tumor model using Calu-6 cells. See Table 23.

d) TH-302 with Carboplatin in a Lung Cancer Model

Inhibition of tumor growth after administration of TH-302 and carboplatin was greater than for either drug individually in an ectopic tumor model using H460 cells. See Table 23.

e) TH-302 with 5FU in a Colon Cancer Model

Inhibition of tumor growth after administration of TH-302 and 5FU was greater than for either drug individually in an ectopic tumor model using HT-29 cells. See Table 23.

f) TH-302 with Doxorubicin in a Soft Tissue Sarcoma Model

Inhibition of tumor growth after administration of the combination TH-302 and doxorubicin of drugs was greater than for either drug individually in an ectopic tumor model using HT1080 cells. See Table 19.

g) TH-302 with Paclitaxel (Taxol) in a Prostate Cancer Model

TH-302 was tested as monotherapy and in combination with Taxol (paclitaxel) in animals bearing highly invasive and metastatic orthotopic prostate cancer PC-3 cells. Animals were randomized into 6 groups of 8 mice each and then treated either with vehicle; Taxol (12 mg/kg, IV, twice a week for 4 consecutive weeks); TH-302 (30 or 50 mg/kg, IP, once a day for 5 days a week for 2 consecutive weeks); or Taxol in combination with TH-302 (using the same single agent regimens). The study demonstrated significant response rates with the combination therapy, at either dose of TH-302, in which disease progression is tracked by tumor volume. Taxol alone and TH-302 alone at either the 30 or 50 mg/kg dose significantly inhibited primary tumor growth during the treatment period. The greatest inhibition of primary tumor growth occurred in the Taxol plus TH-302 combination therapy groups regardless of TH-302 dose, with 4/8 mice (Taxol plus TH-302 at 30 mg/kg) or 3/8 mice (Taxol plus TH-302 at 50 mg/kg) demonstrating a complete response after stringent post-mortem open body fluorescence imaging. Inhibition of tumor growth after administration of the combination of drugs was greater than for either drug individually.

TABLE 23

| | Group | Days to 500 mm$^3$ | Days to 1000 mm$^3$ | TGD500, Days (vs. vehicle) | TGD1000, Days (vs. vehicle) | Ti | Tn | T/C | TGI |
|---|---|---|---|---|---|---|---|---|---|
| TH-302 + | Group 1: Vehicle | 14 | 24 | | | 94.13 | 1171.02 | | |
| Pemetrexed | Group 2: PMX, 150 mg/kg 1/wkx2wks, IP | 19 | 29 | 5 | 5 | 93.89 | 850.21 | 70.2% | 29.8% |
| H460 | Group 3: TH-302, 50 mg/kg 5/wkx2wks, IP | 26 | 34 | 12 | 10 | 93.07 | 507.13 | 38.4% | 61.6% |
| NSCLC | Group 4: TH-302, 50 mg/kg 5/wkx2wks, IP + PMX | 29 | 40 | 15 | 16 | 92.47 | 401.35 | 28.7% | 71.3% |
| TH-302 + | Group 1: Vehicle | 18 | 31 | | | 149.87 | 1069.73 | | |
| Doxorubicin | Group 2: Dox, 4 mg/kg.IV, Q7Dx2 | 27 | 35 | 9 | 4 | 150.86 | 773.97 | 67.7% | 32.3% |
| Calu6 | Group 3: TH-302, 50 mg/kg, IP, QDx5/wkx2wks | 29 | 39 | 11 | 8 | 150.90 | 695.67 | 59.2% | 40.8% |
| NSCLC | Group 4: Dox + TH-302 | 32 | 44 | 14 | 13 | 151.00 | 482.72 | 36.1% | 63.9% |
| TH-302 + | Group 1: Vehicle | 9.5 | 14 | | | 95.8 | 1180.8 | | |
| Carboplatin | Group 2: Carboplatin 20 mg/kg, IV, Q7Dx2 | 11.5 | 18.5 | 2 | 4.5 | 99.0 | 855.6 | 69.7% | 30.3% |
| H460 | Group 3: TH-302, 100 mg/kg, IP, Q7Dx2 | 13.5 | nd | 4 | nd | 97.3 | 706.0 | 56.1% | 43.9% |
| NSCLC | Group 4: TH-302, 150 mg/kg, IP, Q7Dx2 | 14.5 | nd | 5 | nd | 95.8 | 641.6 | 50.3% | 49.7% |
| | Group 5: TH-302, 150 mg/kg + Carboplatin | 18.5 | nd | 9 | nd | 97.3 | 268.8 | 15.8% | 84.2% |
| | Group 6: TH-302, 100 mg/kg + Carboplatin | 19.5 | nd | 10 | nd | 105.7 | 367.3 | 24.1% | 75.9% |
| TH-302 + 5- | Group 1: Vehicle | 22 | 32 | | | 137.21 | 1007.72 | | |
| FU | Group 2: 5-FU, 50 mg/kg, IV, Q3Dx4 | 31 | 43 | 9 | 11 | 139.11 | 514.11 | 43.1% | 56.9% |
| HT29 colon | Group 3: TH-302, 150 mg/kg, IP, Q7Dx3 | 28 | 46 | 6 | 14 | 144.69 | 565.70 | 48.4% | 51.6% |
| cancer | Group 4: TH-302, 100 mg/kg, IP, Q3Dx5 | 29 | 41 | 7 | 9 | 127.82 | 580.55 | 52.0% | 48.0% |
| | Group 5: TH-302, 150 mg/kg (Q7Dx3) + 5-FU | 42 | 57 | 20 | 25 | 136.48 | 289.64 | 17.6% | 82.4% |
| | Group 6: TH-302, 100 mg/kg (Q3Dx5) + 5FU | 39 | 52 | 17 | 20 | 134.08 | 361.60 | 26.1% | 73.9% |

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modifications are intended to be within the scope of the claims appended hereto.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

The invention claimed is:

1. A method of treating cancer comprising administering N,N'-bis(2-bromoethyl)phosphorodamidic acid (1-methyl-2-nitro-1H-imidazol-5-yl)methyl ester (TH-302) and a therapeutically effective dose of an anticancer drug that is not a hypoxia activated prodrug to a patient in need of cancer therapy,
wherein TH-302 is administered intravenously in an amount in the range of 200 mg/m$^2$ to 575 mg/m$^2$ and administration of the anticancer drug that is not a hypoxia activated prodrug begins 30 minutes to 8 hours after administration of TH-302 is completed.

2. The method of claim 1, wherein the drug that is not a hypoxia activated prodrug is administered 1 hour to 6 hours after administration of TH-302 is complete.

3. The method of claim 1, wherein the anticancer drug that is not a hypoxia activated prodrug is docetaxel, paclitaxel, pemetrexed, doxorubicin, gemcitabine, cisplatin, carboplatin or 5-fluorouracil.

4. The method of claim 3 wherein the patient is in need of treatment for lung cancer and the anticancer drug that is not a hypoxia activated prodrug is docetaxel, paclitaxel, pemetrexed, doxorubicin, gemcitabine, 5-fluorouracil, cisplatin, or carboplatin.

5. The method of claim 3 wherein the patient is in need of treatment for prostate cancer and the anticancer drug that is not a hypoxia activated prodrug is docetaxel.

6. The method of claim 3 wherein the patient is in need of treatment for pancreatic cancer and the anticancer drug that is not a hypoxia activated prodrug is gemcitabine.

7. The method of claim 3 wherein the patient is in need of treatment for a soft tissue sarcoma and the anticancer drug that is not a hypoxia activated prodrug is doxorubicin.

8. The method of claim 3 wherein the patient is in need of treatment for cancer of the colon and the anticancer drug that is not a hypoxia activated prodrug is cisplatin or 5-fluorouracil.

9. The method of claim 1, wherein the TH-302 is administered for two or more four-week cycles, each cycle comprising administering TH-302 once weekly for 3 consecutive weeks followed by a week of no TH-302 administration, or is administered for two or more three-week cycles, each cycle comprising administering TH-302 once weekly for 2 consecutive weeks followed by a week of no TH-302 administration.

10. The method of claim 1, wherein the patient is treated prophylactically with a topical agent to reduce or prevent mucosal and/or skin damage.

11. A pharmaceutical formulation comprising TH-302 as an active ingredient in an amount of about 50 mg/ml to about 300 mg/ml, a nonionic surfactant in an amount effective to act as a stabilizer, and ethanol as a carrier.

12. The pharmaceutical formulation of claim 11, wherein the nonionic surfactant is sorbitan mono-oleate polyoxyethylene (TWEEN 80).

13. The pharmaceutical formulation of claim 12, comprising 60 mg/ml TH-302, 95% (v/v) ethanol, and 5% TWEEN 80.

14. The pharmaceutical formulation of claim 12, further comprising dimethylacetamide.

15. The method of claim 1, wherein TH-302 is administered in an amount in the range of about 240 mg/m$^2$ to about 575 mg/m$^2$.

16. The method of claim 6, wherein TH-302 is administered in an amount in the range of about 240 mg/m$^2$ to about 575 mg/m$^2$.

17. The method of claim 7, wherein TH-302 is administered in an amount in the range of about 240 mg/m$^2$ to about 575 mg/m$^2$.

18. The method of claim 8, wherein TH-302 is administered in an amount in the range of about 240 mg/m$^2$ to about 575 mg/m$^2$.

* * * * *

UNITED STATES PATENT AND TRADEMARK OFFICE
CERTIFICATE OF CORRECTION

| | |
|---|---|
| PATENT NO. | : 8,946,275 B2 |
| APPLICATION NO. | : 13/125303 |
| DATED | : February 3, 2015 |
| INVENTOR(S) | : Curd et al. |

Page 1 of 1

It is certified that error appears in the above-identified patent and that said Letters Patent is hereby corrected as shown below:

Title Page, (75) Inventors should read: John G. Curd, Burlingame, CA (US); Karen Curd, legal representative, Burlingame, CA (US); Stewart Kroll, Oakland, CA (US); Mark Matteucci, Portola Valley, CA (US); Charles P. Hart, Mountain View, CA (US); Jian-Xin Duan, South San Francisco, CA (US); Jessica D. Sun, Fremont, CA (US).

Signed and Sealed this
Twentieth Day of October, 2015

Michelle K. Lee
*Director of the United States Patent and Trademark Office*